(12) United States Patent
Adams

(10) Patent No.: US 8,162,902 B2
(45) Date of Patent: Apr. 24, 2012

(54) SYSTEMS AND METHODS FOR PROVIDING AN AUTOMATIC OCCLUSION DEVICE

(75) Inventor: Chad M. Adams, Cedar Hills, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 6 days.

(21) Appl. No.: 12/418,467

(22) Filed: Apr. 3, 2009

(65) Prior Publication Data
US 2009/0254049 A1 Oct. 8, 2009

Related U.S. Application Data

(60) Provisional application No. 61/042,522, filed on Apr. 4, 2008, provisional application No. 61/078,810, filed on Jul. 8, 2008.

(51) Int. Cl.
*A61M 5/00* (2006.01)
(52) U.S. Cl. ........................................ 604/247
(58) Field of Classification Search .............. 604/246, 604/247, 523, 118, 132
See application file for complete search history.

(56) References Cited

U.S. PATENT DOCUMENTS

| 4,476,888 | A | 10/1984 | Lachmann et al. |
| 4,911,403 | A | 3/1990 | Lockwood, Jr. |
| 5,249,598 | A | 10/1993 | Schmidt |
| 5,586,629 | A | 12/1996 | Shoberg et al. |
| 6,152,898 | A | 11/2000 | Olsen |
| 2005/0165364 | A1 | 7/2005 | DiMatteo et al. |
| 2005/0273083 | A1 | 12/2005 | Lebel et al. |
| 2006/0149189 | A1 | 7/2006 | Diamond et al. |
| 2007/0204922 | A1* | 9/2007 | Owczarczak ............ 137/601.19 |
| 2007/0272311 | A1* | 11/2007 | Trocki et al. ............... 137/601.2 |

FOREIGN PATENT DOCUMENTS

| DE | 20 2007 003 817 U1 | 7/2007 |
| EP | 0 947 752 A1 | 10/1999 |
| EP | 1 897 585 A1 | 12/2008 |

* cited by examiner

*Primary Examiner* — Jackie Ho
*Assistant Examiner* — Imani Hayman
(74) *Attorney, Agent, or Firm* — Mony R. Ghose; Kirton & McConkie

(57) ABSTRACT

An auto-occlusion safety device is provided for use in preventing rupture of infusion components during rapid infusion procedures. An occlusion valve is disclosed having a threshold pressure that is less than a rupture tolerance of the infusion system components. As the fluid pressure of the infusion system increases beyond the threshold pressure of the occlusion valve, the occlusion valve is automatically activated thereby occluding fluid flow upstream from a vulnerable infusion component. An accumulator is further disclosed for use in combination with the safety device to compensate for time delays in full activation of the occlusion valve.

27 Claims, 24 Drawing Sheets

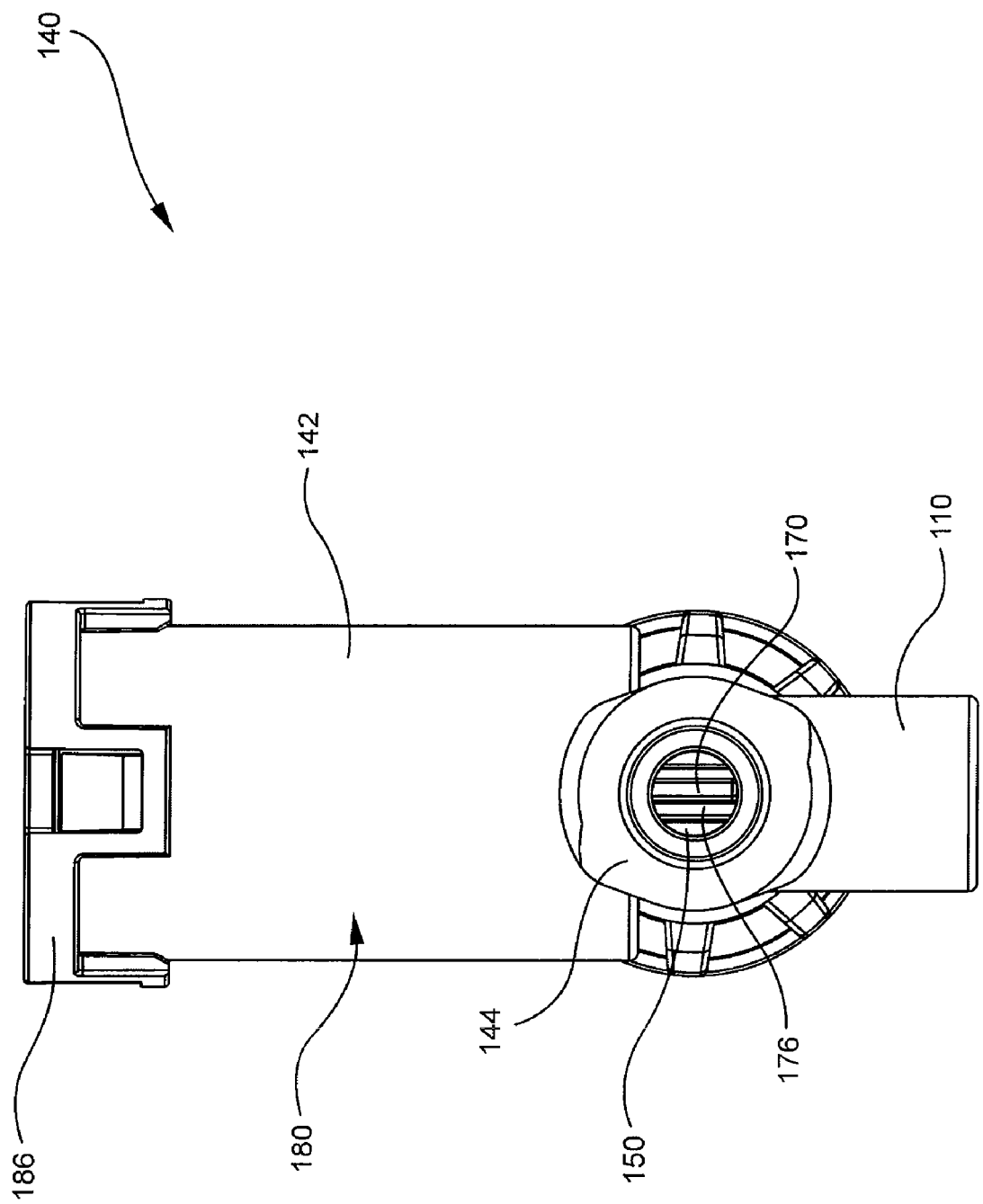

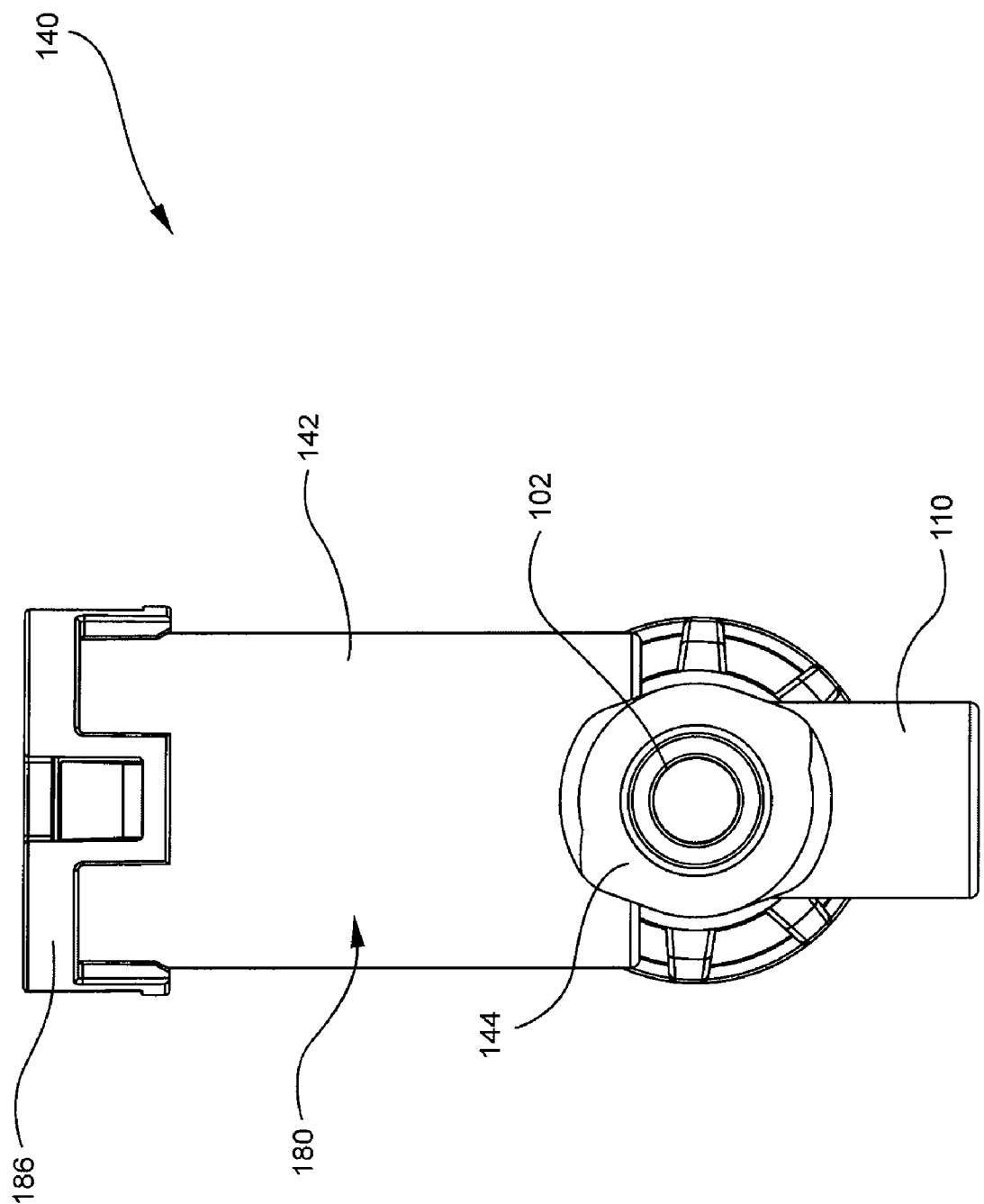

SYSTEMS AND METHODS FOR PROVIDING AN AUTOMATIC OCCLUSION DEVICE

RELATED APPLICATIONS

This application claims the benefit of U.S. Provisional Application No. 61/042,522, filed Apr. 4, 2008, entitled IN-LINE POWER INJECTION SAFETY DEVICE FOR PIVC AND PICC APPLICATIONS, and U.S. Provisional Application No. 61/078,810, filed Jul. 8, 2008, entitled IN-LINE POWER INJECTION SAFETY DEVICE FOR PIVC, CVC, PORT & PICC APPLICATIONS WITH ENERGY ASSIST FEATURE TO REDUCE PRESSURE REACTION TIME, both of which are incorporated herein by reference.

BACKGROUND OF THE INVENTION

The present invention relates generally to vascular infusion systems and components, including catheter assemblies and devices used with catheter assemblies. In particular, the present invention relates to safety devices configured to prevent rupture of infusion components due to excessive fluid pressure within a vascular infusion system.

Vascular access devices are used for communicating fluid with the anatomy of a patient. For some diagnostic procedures, a vascular access device is used for infusing a contrast media into the vascular system of a patient. The contrast material is generally radiopaque thereby enabling diagnosis of various parameters of the patient's vascular system via CT or MRI scan imaging.

A trend in diagnostic imaging procedures is to enhance visualization by increasing the viscosity and the injection rate of the contrast media. These rapid infusion methods produce enhanced bolus density of the injected contrast media resulting in improved image quality. However, these methods also generate increased pressure within vascular access devices resulting in the increased likelihood of infusion component rupture. Additionally, line patency is often compromised by patient or catheter position, as well as flow rate induced kinking also leading to increased pressure within the various vascular access devices.

As a result of these challenges, the Food and Drug Administration has received numerous adverse event reports in which vascular access devices have ruptured when used with power injectors to administer contrast media as part of CT studies. The ruptured devices have included peripheral catheters, central venous catheters, implanted ports, extension tubing, and intravenous administration sets. Many of these ruptures have resulted in device fragmentation, embolism or migration requiring surgical intervention, extravasations of contrast media, loss of venous access requiring device replacement, physical injury to the patient, and contamination of room and personnel with blood and contrast media.

Accordingly, the problem of excessive pressure buildup during rapid infusion procedures remains to be solved. Thus, the present disclosure presents systems and methods to prevent undesirable rupture of infusion components, as is commonly experienced during rapid infusion procedures.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient rapid infusion procedures.

One aspect of the present invention provides an auto-occlusion safety device for use in vascular rapid infusion systems. The safety device is generally placed upstream from an infusion component, such as an intravenous catheter or an extension set. The safety device further includes an occlusion valve having a threshold pressure less than the rupture capacity of an infusion component of the infusion system. The device also serves as a pressure regulator within the system. Thus, in the event that the fluid pressure within the infusion system exceeds the threshold pressure of the occlusion valve, the occlusion valve is automatically activated resulting in an occlusion of the infusion system at a point upstream from the vulnerable infusion component(s). Thus, "automatic" activation can be defined as the activation of the valve without a required user input or action.

In some embodiments, the occlusion valve includes a piston partially disposed in a compression chamber. As the fluid pressure within the infusion system increases, a lower portion of the compression chamber fills with infusant causing the piston to move upwardly within the compression chamber. As the piston moves upwardly, a portion of the piston positioned exterior to the compression chamber is repositioned within the safety device to occlude the fluid pathway of the infusion system.

In some aspects of the present invention, a compression spring is interposedly positioned between the piston and the compression chamber, such that the portion of the piston disposed in the compression chamber is biased towards the lower portion of the compression chamber. Thus, when the fluid pressure within the infusion system exceeds the threshold pressure of the valve or compression spring, the piston moves upwardly within the compression chamber thereby compressing the compression spring. When the fluid pressure decreases to less than the threshold pressure of the valve, the compression spring relaxes thereby returning the piston to an inactivated, non-occluding position within the safety device.

The piston may further include a locking mechanism configured to engage an inner surface of the compression chamber, following activation of the valve. In this manner, the activated or occluding position of the piston is maintained regardless of a subsequent decrease of fluid pressure within the infusion system. Thus, the locking mechanism prevents the piston from returning to an inactivated or non-occluding position following automatic activation of the safety device.

In some embodiments, the safety device further includes a visual indicator to signal that the valve has been activated hence a failed infusion procedure. The indicator may include a portion of the valve that is repositioned following activation of the valve. In some embodiments, a casing of the valve includes a window through which a user may visualize the repositioned portion of the valve. In other embodiments, a portion of the valve is repositioned external to the valve casing, thereby indicating an activation event.

Finally, in some embodiments an accumulator is used in combination with an auto-occlusion safety device, as part of an infusion system in accordance with the present invention. The accumulator generally includes any device capable of diverting and retaining infusant within an infusion system, in response to increased fluid pressure. The accumulator provides additional time for the system to shut down. The accumulator is configured to have a threshold pressure that is generally less than the threshold pressure of the auto-occlusion valve. As such, when fluid pressure within the infusion system increases rapidly, the accumulator reduces the rate of pressure increase within the infusion system thereby compensating for any delay in time required for complete activation of the auto-occlusion valve.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 2D is a plan end view of an inactivated auto-occlusion safety device in accordance with a representative embodiment of the present invention.

FIG. 2F is a plan end view of an activated auto-occlusion safety device in accordance with a representative embodiment of the present invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1A:
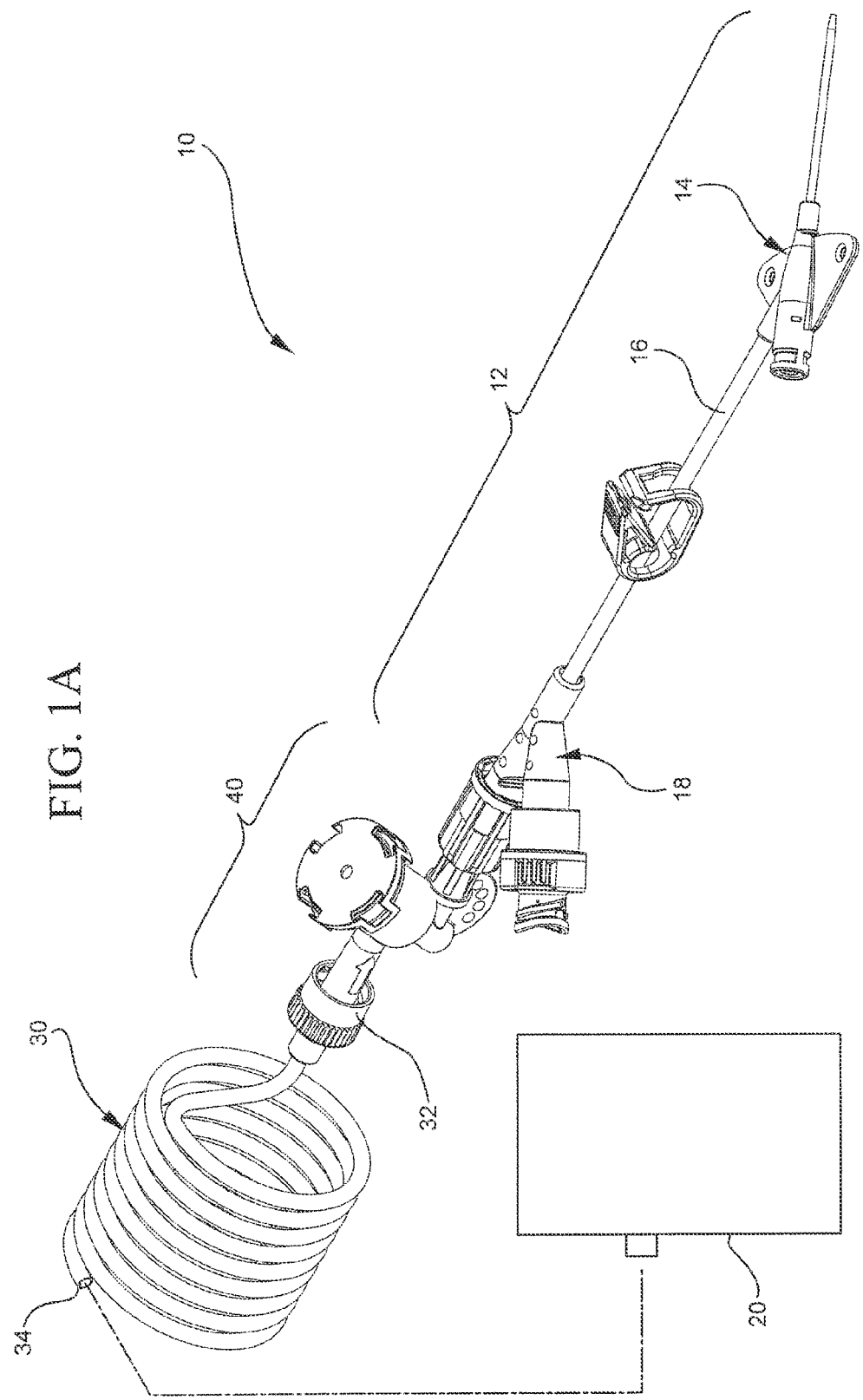
FIG. 1A is a perspective view of an infusion system in accordance with a representative embodiment of the present invention.

Referring now to FIG. 1A, a vascular infusion system 10 is shown. Systems of this type operate at up to 2000 psi. Many systems operate in the range of 75 to 2000 psi, specific devices of this type operate at 100, 200, and 300 psi. The vascular infusion system 10 comprises a vascular access device 12 coupled to an injector pump 20 via a coiled extension set 30. The infusion system 10 further comprises an auto-occlusion safety device 40 positioned between the vascular access device 12 and the injector pump 20. In some embodiments, the safety device 40 is interposed between the coiled extension set 30 and the vascular access device 12. In other embodiments, the safety device 40 is interposed between the injector pump 20 and the coiled extension set 30. Finally, in some embodiments, one of the components 12, 20, and 30 of the vascular access system 10 is modified to incorporate an auto-occlusion safety device 40, in accordance with the teachings of the present invention.

The vascular access device 12 generally comprises an intravenous catheter 14. A desired infusant is typically delivered to the catheter 14 via a section of intravenous tubing 16 coupled to the catheter 14. In some embodiments, a y-adapter 18 is coupled to an end of the tubing 16 opposite the catheter 14, enabling the vascular access device 12 to be coupled to the remainder of the vascular infusion system 10. One of skill in the art will appreciate the possible variations and specific features of available vascular access devices 12, as are commonly used in the medical and research professions. For example, in some embodiments a catheter incorporating a diffuser is utilized in a vascular infusion system 10 in accordance with the present invention.

The injector pump 20 generally comprises a fluid pumping apparatus configured to rapidly deliver an infusant, such as blood, medicaments, and CT scan contrast agents to a patient's vascular system. Desirable infusants may also include various fluids often of high viscosity as required for medical and diagnostic procedures. In some embodiments, the injector pump 20 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 20 and a vascular access device 12 are selected to compatibly achieve a desired infusion flow rate.

The coiled extension set 30 generally comprises a flexible or semi-flexible polymer tubing configured to deliver an infusant from the injector pump 20 to the vascular access device 12. The extension set 30 includes a first coupler 32 for connecting the extension set 30 to a downstream device 12 or 40. The extension set 30 also includes a second coupler 34 for connecting the extension set 30 to the injector pump 20. The coiled configuration of the extension set 30 generally prevents undesirable kinking or occlusion of the set 30 during infusion procedures. However, one of skill in the art will appreciate that the extension set 30 may include any configuration capable of efficiently delivering an infusant from the injector pump 20 to the patient via a vascular access device 12.

The auto-occlusion safety device 40 is generally positioned upstream from the vascular access device 12 so as to be interposed between the vascular access device 12 and the infusion pump 20. The safety device 40 is configured to permit flow of an infusant through the infusion system 10 at fluid pressures that are less than the failure strengths of the various components 12, 20, 30 and 40 of the infusion system 10. In the event that a fluid pressure within the infusion system 10 nears or exceeds the failure strength of an infusion component, the safety device 40 automatically occludes the fluid pathway through the infusion system 10, thereby preventing undesirable rupture of the system components. Therefore, "automatic" activation can be defined as the activation of the valve without a required user input or action. Thus, the safety device 40 enables a user to increase the flow rate of an infusant through the vascular infusion system 10 without concern of device complications or rupture.

Currently, infusion components 12 and 30 limit the allowable flow rate of an infusion system 10 based on the device rupture capability, which is dramatically influenced by infusant viscosity, density, and internal dimensions of the system components 12 and 30. The maximum specified infusant flow rate for the infusion components is dictated by the most viscous infusant that could forseeably be used in an open flow state (i.e. a non-occluded condition), which ultimately minimizes the flow rate that could be achieved for these devices 12 and 30 in a safe manner for all other infusants of lower viscosity. A particular concern among manufacturers is use of infusion components with contrast media. A specification impact based on contrast media viscosity and device pressure capability for a 4 F×55 cm single lumen peripheral inserted central catheter (PICC) utilizing warmed contrast media is outlined in Table 1.

TABLE 1

| Contrast | Concentration | Viscosity (poise) 20° C. | Viscosity (poise) 25° C. | Viscosity (poise) 37° C. | Density (kg/m³) | Actual Pump Pressure at Prescribed IFU Flow Rate of 5 ml/sec (psi) | Actual Device Pressure at Prescribed IFU Flow Rate of 5 ml/sec (psi) | Flow Rate Reduction Due to VAD of Pump IFU Specification w/Heated Media (ml/sec) | Restricted By |
|---|---|---|---|---|---|---|---|---|---|
| (GE) Omnipaque | 300 | 0.12 | — | 0.06 | 1346.30 | 137.00 | 107.00 | 3.60 | Device |
|  | 350 | 0.20 | — | 0.11 | 1403.19 | 246.00 | 193.00 | 0.50 | Device |
| (Bracco) Isovue | 300 | 0.09 | — | 0.05 | 1336.32 | 115.00 | 90.00 | 2.25 | Device |
|  | 370 | 0.21 | — | 0.09 | 1402.19 | 203.00 | 158.00 | 1.50 | Device |
| (Covidien) Optiray | 320 | — | 0.10 | 0.06 | 1368.26 | 137.00 | 107.00 | 3.60 | Device |
|  | 350 | — | 0.14 | 0.09 | 1402.19 | 202.00 | 158.00 | 1.50 | Device |
| (GE) Visipaque (Kidney Friendly) | 270 | 0.13 | — | 0.06 | 1369.00 | 137.00 | 107.00 | 3.40 | Device |
| (Schering) Ultravist | 300 | 0.09 | — | 0.05 | 1330.00 | 114.00 | 89.80 | 2.30 | Device |
|  | 370 | 0.22 | — | 0.10 | 1409.00 | 225.00 | 176.00 | 1.10 | Device |

As previously discussed, the trend in diagnostic imaging procedures is to utilize contrast media enhancement demanding more viscous contrast media be pushed at higher flow rates to enhance bolus density and image quality. This of course generates higher fluid pressure within the infusion system 10 resulting in the increased likelihood of device rupture if the recommended specifications are not decreased. Additional decreases in the pressure capabilities further broadens the gap in unmet clinical and customer needs.

Figure 1B:
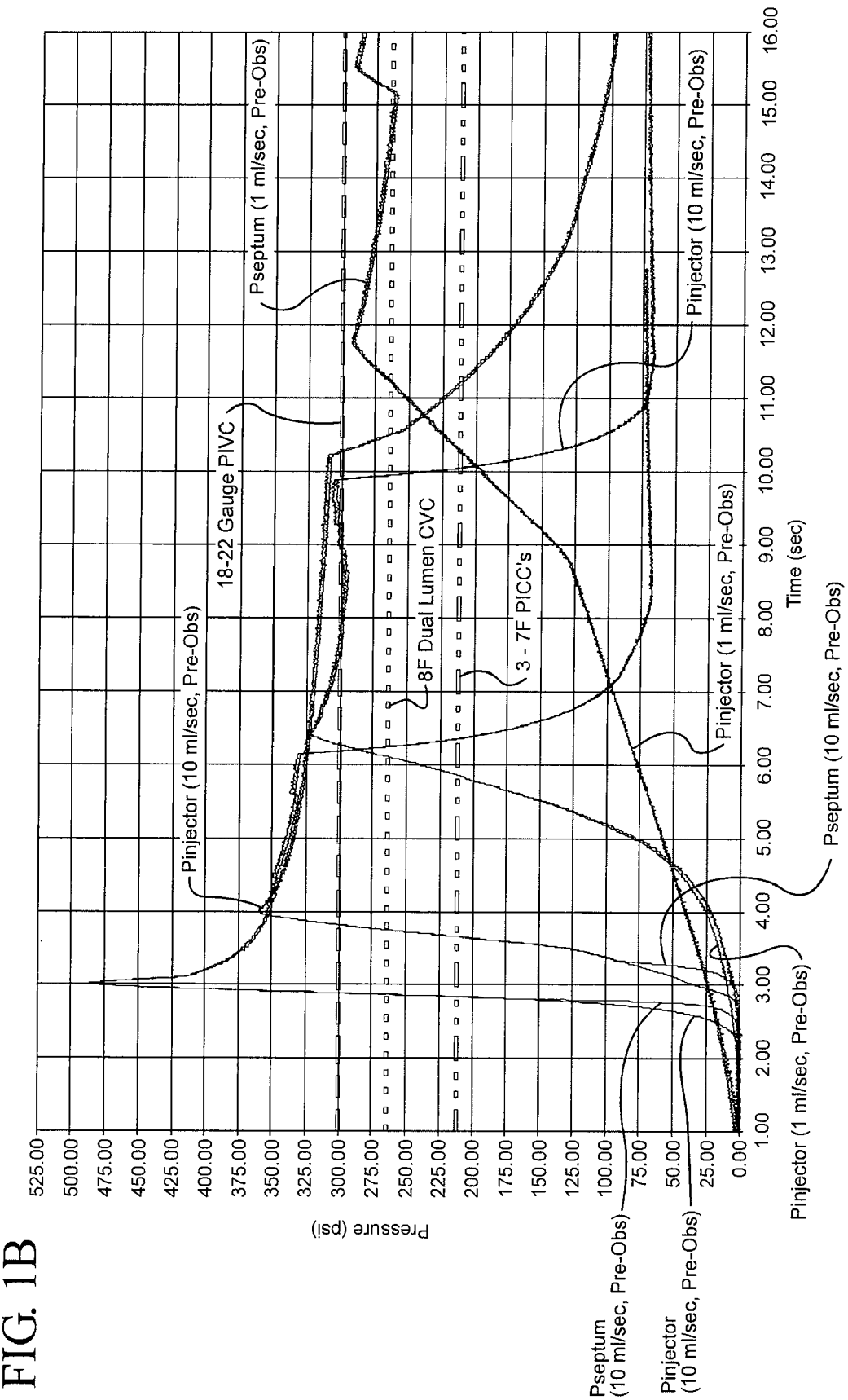
FIG. 1B is a chart demonstrating pressure response times for various occluded infusion components in accordance with representative embodiments of the present invention.

In addition, line patency is often compromised by patient or catheter position and flow rate induced kinking. Kinking of the infusion system 10 results in static pressures (i.e. a non-open flow condition) that exceed the capacity of the infusion components 12 and 30. One having skill in the art will appreciate that this condition occurs in all vascular access devices, including products specifically designed contrast enhanced CT procedures, including PICCs, central venous catheters (CVCs), and ports. Therefore, a substantial gap exists between infusion component pressure capabilities in an occluded state or when non-heated media is utilized for PICCs/CVCs versus what injector pumps actually delivered, as shown in FIG. 1B.

The auto-occlusion safety device 40 of the present invention is generally configured to prevent fluid pressures within the infusion system 10 from exceeding rupture capacity of the infusion components 12 and 30. In some embodiments, safety device 40 includes a pressure sensitive valve that is triggered when a pressure within the infusion system 10 exceeds a threshold pressure of the valve. Upon activation of the pressure sensitive valve, the fluid flow upstream from the safety device 40 is occluded thereby preventing rupture of infusion components 12 downstream from the safety device 40. In this way, the safety device 40 acts as a hydraulic "fuse" to prevent a rupture from occurring within the vascular infusion system 10. Therefore, in some embodiments where infusion components are positioned upstream from the safety device 40, the rupture capacity of the coiled extension set is selected to exceed the threshold pressure of the pressure sensitive valve.

The auto-occlusion safety device 40 of the present invention may be configured in various embodiments to accomplish the intended purposes as disclosed herein. Non-limiting examples of the safety device 40 are shown in FIGS. 2A-5B, below. However, one of skill in the art will appreciate that the feature and workings of the safety device 40 may be modified to achieve similar results, and therefore such modifications are included and anticipated as possible embodiments of the present invention.

Figure 2A:
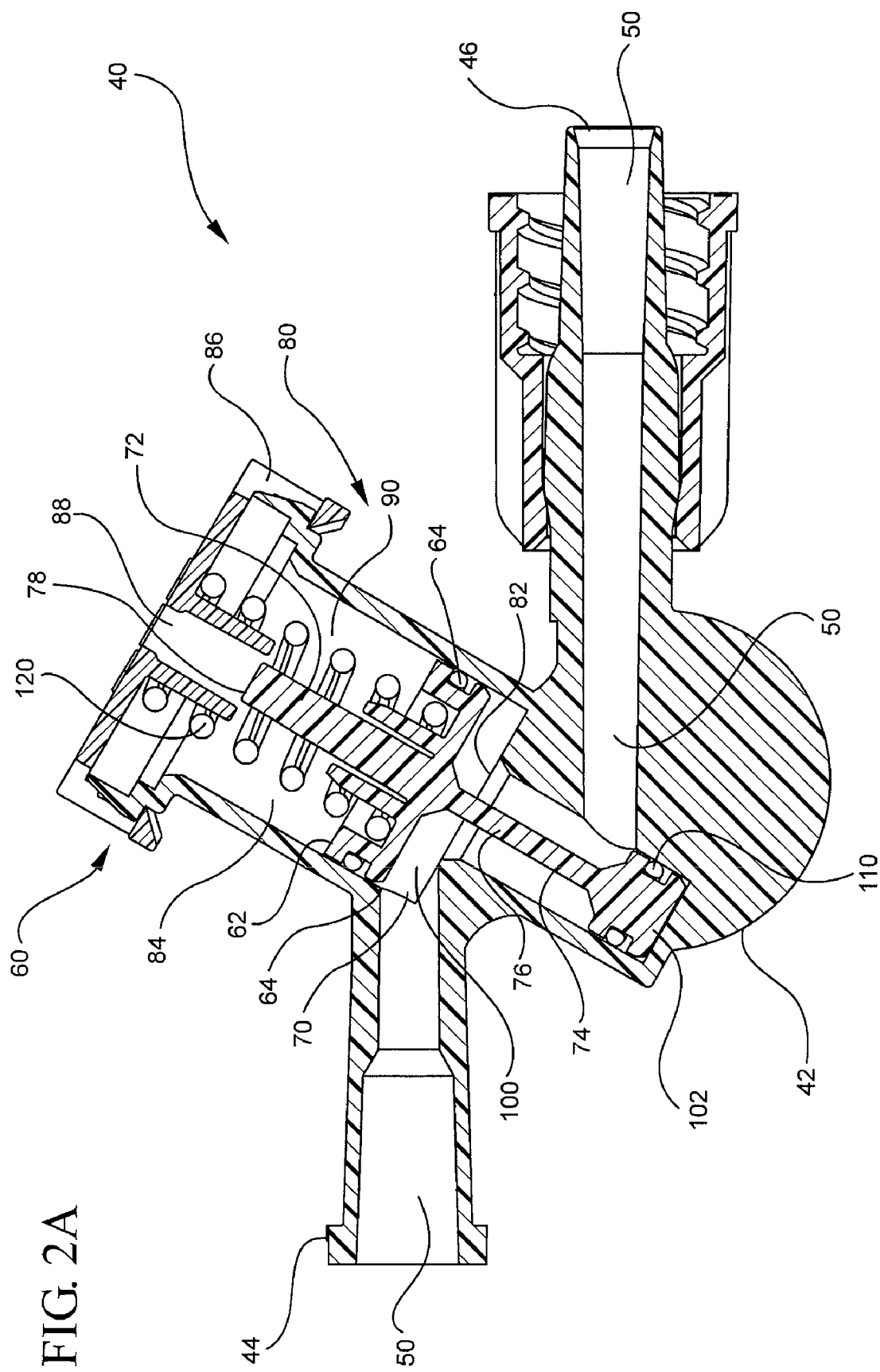
FIG. 2A is a cross-section side view of an inactivated auto-occlusion safety device in accordance with a representative embodiment of the present invention.

Referring now to FIG. 2A, an auto-occlusion safety device 40 is shown in an open flow, or inactivated position. The safety device 40 comprises a z-shaped outer casing 42 having an inlet port 44 and an outlet port 46. A fluid pathway 50 is provided such that an infusant may enter into the safety device 40 via the inlet port 44 and exit the safety device 40 via the outlet port 46.

The safety device 40 further comprises a pressure sensitive valve 60. The valve 60 generally comprises a portion of the casing 42 and is interposingly positioned between the inlet port 44 and the outlet port 46 of the safety device 40. In some embodiments, the valve 60 comprises a compression chamber 80 which houses various components of the valve 60. A bottom wall 82 of the compression chamber 80 is generally configured to abut the fluid pathway 50. In some embodiments, the bottom wall 82 is in fluid communication with the fluid pathway 50 such that a fluid pressure within the compression chamber 80 is equal to a fluid pressure within the fluid pathway 50.

The compression chamber 80 comprises an upper chamber 90 and a lower chamber 100. The upper and lower chambers 90 and 100 are defined by a plunger 62 slidably positioned within the compression chamber 80. A seal 64 is positioned between the plunger 62 and an inner wall surface 84 of the compression chamber 80 so as to prevent an infusant within the fluid pathway 50 from bypassing the plunger 62 into the upper chamber 90 of the compression chamber 80. In some embodiments, the seal 64 is an o-ring inserted into a groove circumscribing an outer perimeter of the plunger 62.

The plunger 62 is fixedly coupled to a piston 70. The piston 70 comprises a first end 72 and a second end 74, and a middle portion supporting the plunger 62. The first end 72 of the piston 70 is entirely positioned within the upper chamber 90 of the valve 60. The second end 74 of the piston 70 extends from the plunger 62, through the lower chamber 100 of the valve 60 and into the fluid pathway 50. In some embodiments, a terminal end 102 of the second end 74 of the piston 70 is temporarily housed within a housing chamber 110 of the fluid pathway 50.

A shaft portion 76 of the piston 70 is generally positioned in the portion of the fluid pathway between the inlet port 44 and the outlet 46. As such, the width and/or diameter of the shaft portion 76 is configured to be less than the diameter of the fluid pathway 50. As such, an infusant within the fluid pathway 50 is able to bypass the shaft portion 76 of the piston 70 without obstruction.

The compression chamber 80 further comprises a cap or lid 86. The lid 86 seals the top end of the compression chamber 80 such that the upper chamber 90 of the compression chamber 80 is defined by the portion of the compression chamber between the plunger 62 and the lid 86. In some embodiments, the lid 86 comprises a one-way air valve (not shown) such that as pressure increases within the upper chamber 90 of the compression chamber, excess pressure within the upper chamber 90 is released via the air valve.

As fluid pressure increases within the fluid pathway 50, the plunger 62 is driven upward into the compression chamber 80, effectually decreasing the volume of the upper chamber 90. As the plunger 62 moves further into the compression chamber 80 the piston 70 also translates within the compression chamber 80 and the fluid pathway 50. In some embodiments, a compression spring 120 is disposed in the upper chamber 90 between the plunger 62 and the lid 86. Thus, as the plunger 62 moves further into the compression chamber 80, the compression spring 120 is compressed to a pressure equal to the fluid pressure within the fluid pathway 50.

Figure 2B:
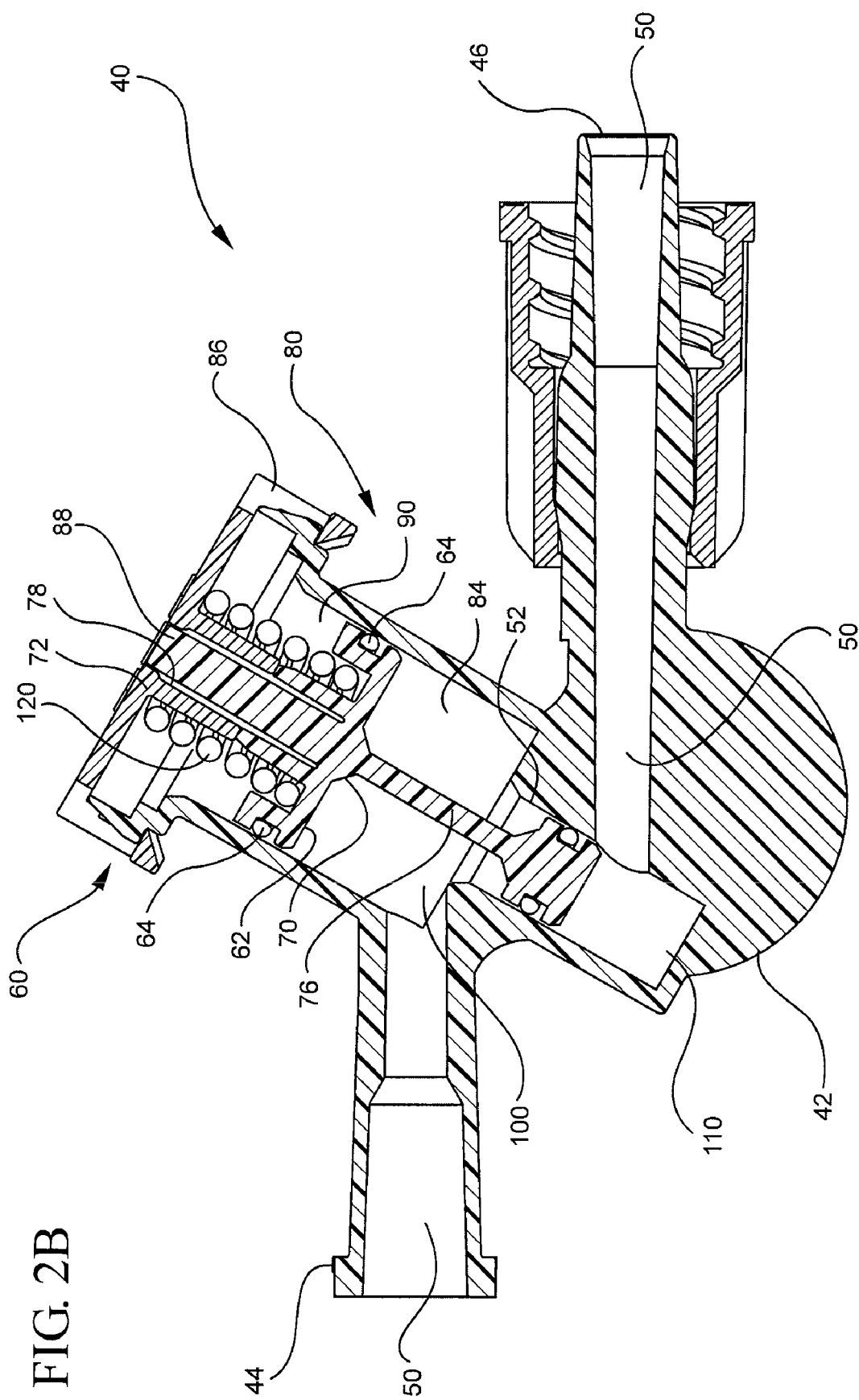
FIG. 2B is a cross-section side view of an activated auto-occlusion safety device in accordance with a representative embodiment of the present invention.

Referring now to FIG. 2B, the auto-occlusion safety device 40 of FIG. 2A is shown in a closed flow, or activated position. As the fluid pressure increases within the fluid pathway 50, the plunger 62 is driven upward into the compression chamber 80, as shown. The activated position of the safety device 40 reduces the volume of the upper chamber 90 and increases the volume of the lower chamber 100. As such, the compression spring 120 within the upper chamber 90 is compressed with a pressure equal to the fluid pressure within the fluid pathway 50.

As the first end 72 of the piston 70 moves upwardly with the plunger 62, the terminal end 102 of the piston 70 is simultaneously removed from the housing chamber 110 and repositioned within the fluid pathway 50. Unlike the shaft portion 76 of the piston 70, the terminal end 102 of the piston 70 is configured to comprise a width that substantially blocks or occludes the fluid pathway 50. Thus, as the fluid pressure increases within the fluid pathway 50, the plunger 62 is moved upward thereby repositioning the terminal end 102 of the piston into the fluid pathway 50 resulting in an occlusion of the fluid pathway 50. In some embodiments, a seal 64 is further positioned between the terminal end 102 of the piston 70 and an inner wall surface 52 of the fluid pathway 50, so as to prevent an infusant from bypassing the terminal end 102 of the piston 70. For example, in some embodiments the seal 64 is an o-ring inserted into a groove circumscribing an outer perimeter of the terminal end 102.

The occluding effect of the repositioned terminal end 102 isolates downstream infusion components 12 from the dangerously high fluid pressures upstream from the piston 70. The valve 60 remains in an activated position until the fluid pressure upstream from the piston 70 returns to a pressure less than the threshold pressure of the valve 60. As the fluid pressure upstream from the piston 70 decreases, the compensation spring 120 relaxes thereby returning the valve 60 to an inactivated or open flow position, as shown in FIG. 2A. Thus, in some embodiments, the pressure sensitive valve 60 automatically activates and resets in response to the fluid pressure within the fluid pathway 50.

In some embodiments, lid 86 further comprises a window 88. The window 88 is configured so as to receive a tip portion 78 of the piston 70 when the valve 60 is activated. The tip portion 78 is viewed through the window 88 to indicate to a user that the valve 60 is in an activated position. Thus, the tip portion 78 and the window 88 provide a visual indicator of an activated or inactivated state of the safety device 40.

Figure 2C:
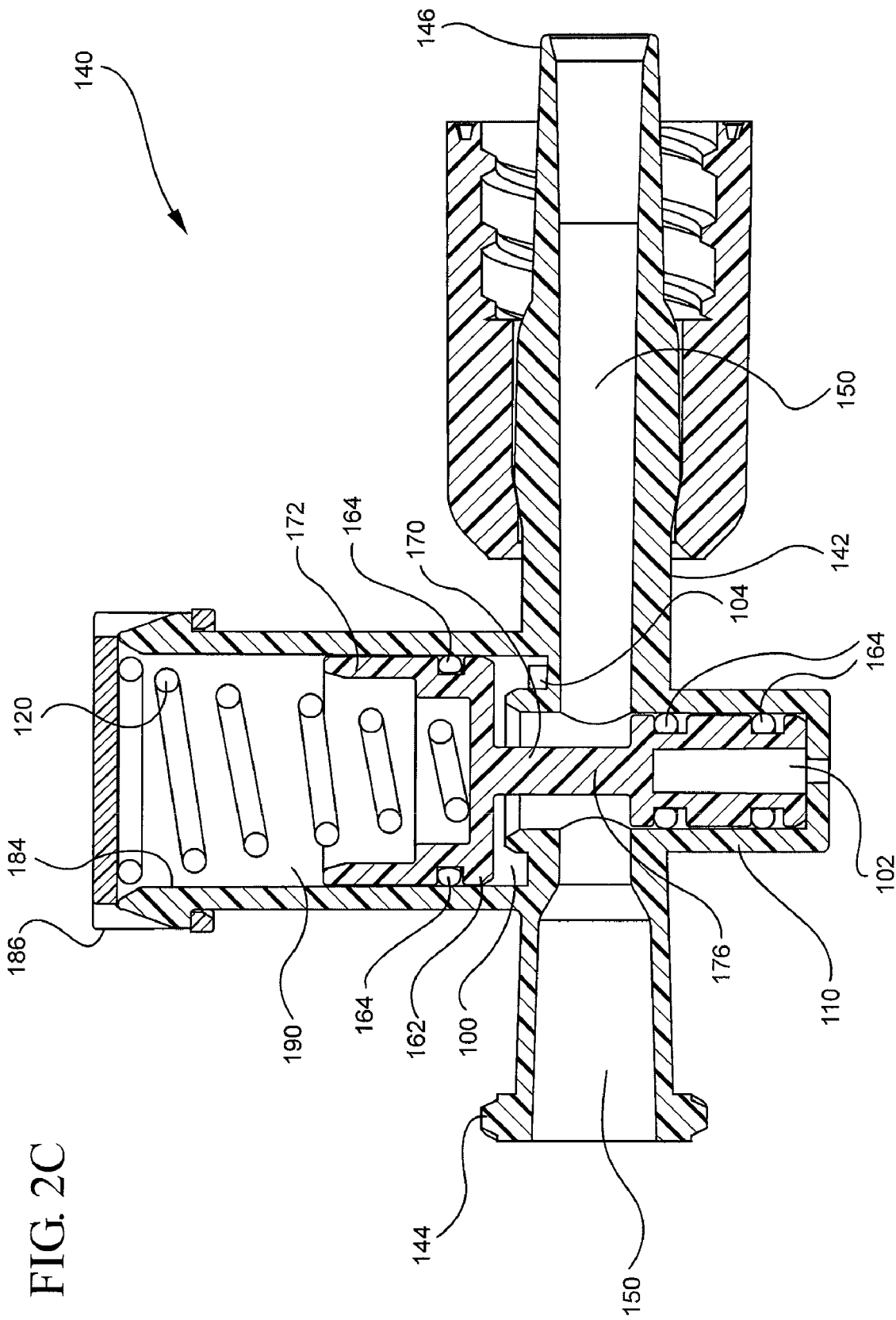
FIG. 2C is a cross-section side view of an inactivated auto-occlusion safety device in accordance with a representative embodiment of the present invention.

Referring now to FIG. 2C, a cross-sectioned view of an auto-occlusion safety device 140 is shown in an inactivated or open flow position. Parts corresponding to those previously described are designated with similar reference numbers beginning with 100. In some embodiments, the safety device 140 comprises a t-shape configuration. For this configuration, the first end 172 of the piston 170 is modified to serve as both a plunger and a cup for supporting the compression spring 120. A seal 164 is positioned between an outer surface of the first end 172 and an inner wall surface 184 of the compression chamber 180 so as to prevent an infusant within the fluid pathway 150 from bypassing the first end 172 of the piston 170 into the upper chamber 190 of the compression chamber 180.

A lower chamber 100 is configured to include a fluid channel 104 located within a portion of the fluid pathway 150 downstream from the piston 170. Thus, as the fluid pressure within the fluid pathway 150 increases, fluid is driven into the lower chamber 100 via the fluid channel 104. As the pressure increases beyond the threshold pressure of the compression spring 120, the compression spring 120 compresses and the terminal end 102 of the piston 170 is repositioned within the fluid pathway 150, as shown in FIG. 2E.

With reference to FIG. 2D, a rear perspective view of the auto-occlusion safety device 140 is shown. As with the previous embodiment, a shaft portion 176 of the piston 170 is configured to have a width or diameter that is less than the diameter of the fluid pathway 150. As such, an infusant entering the safety device 140 through the inlet port 144 may easily bypass the piston 170 and exit the outlet port (not shown) without obstruction.

Figure 2E:
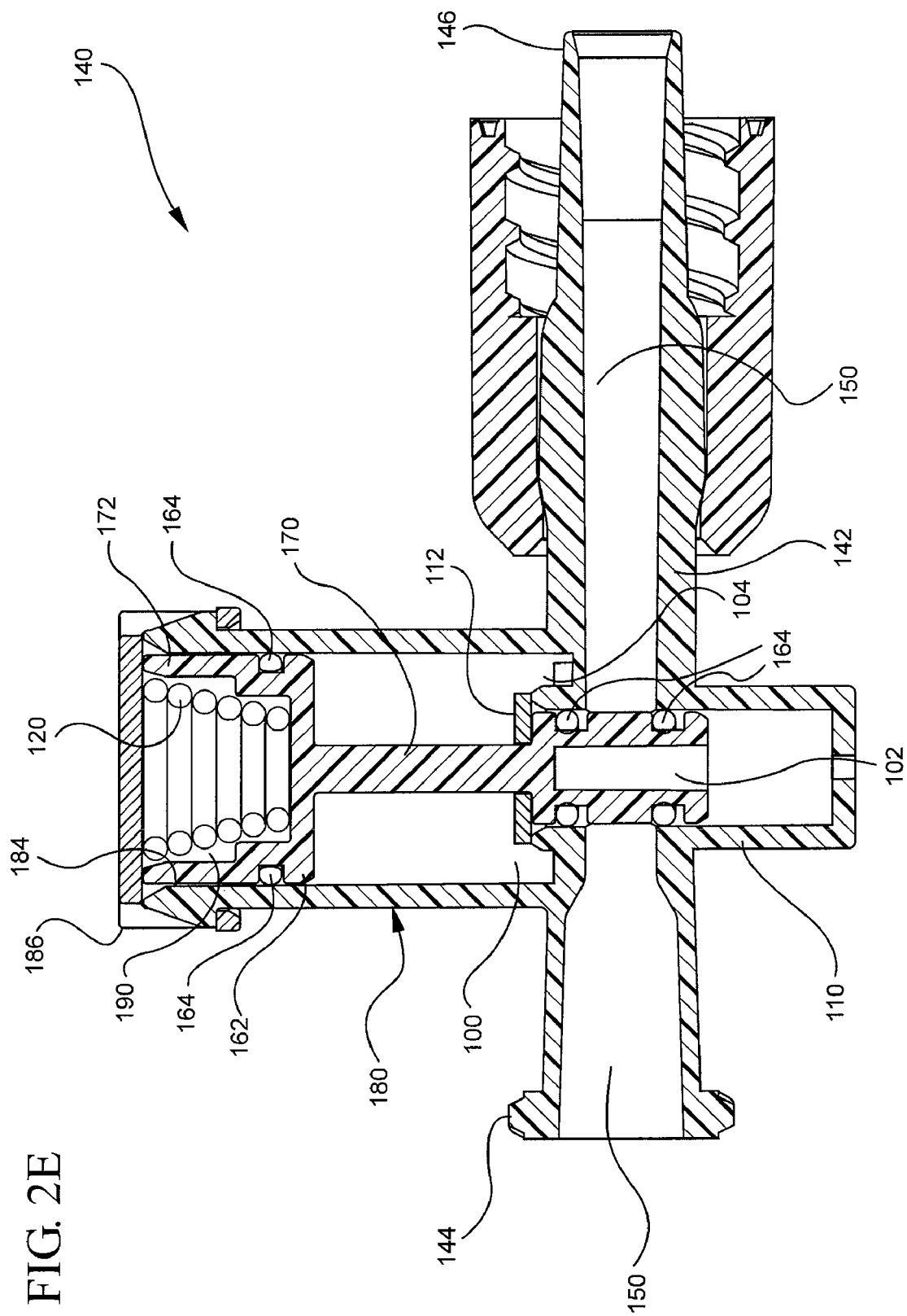
FIG. 2E is a cross-section side view of an activated auto-occlusion safety device in accordance with a representative embodiment of the present invention.

With reference to FIG. 2E, a cross-sectioned view of an activated safety device 140 is shown. As the pressure within the fluid pathway 150 increases, the infusant is forced into the lower chamber 100 of the compression chamber 180 thereby forcing the first end 172 of the piston 170 upward into the compression chamber 180. As a result, the volume of the upper chamber 190 decreases and the volume of the lower chamber 100 increases. As the piston 170 moves upwardly, the terminal end 102 of the piston 170 is partially removed from the housing chamber 110 and repositioned into the fluid pathway 150.

In some embodiments, a recess 112 is provided in the fluid pathway 150 opposite the housing chamber 110. The recess 112 is configured to compatibly receive an upper portion of the terminal end 102 such that a perimeter edge of the terminal end 102 overlaps the fluid pathway 150, effectually blocking or occluding the fluid pathway 150. In some embodiments, a seal 164 is positioned both between the terminal end 102 housing chamber 110, and between the terminal end 102 and the recess 112. As shown in FIG. 2F, when activated, the terminal end 102 completely blocks the fluid pathway 150 to prevent additional passage of infusant. Thus, the repositioned terminal end 102 prevents further increases in fluid pressure downstream from the piston 170. As fluid pressure decreases downstream from the piston 170, the compression spring 120 relaxes and automatically returns the terminal end 102 of the piston 170 to an inactivated or open flow position.

Figure 3A:
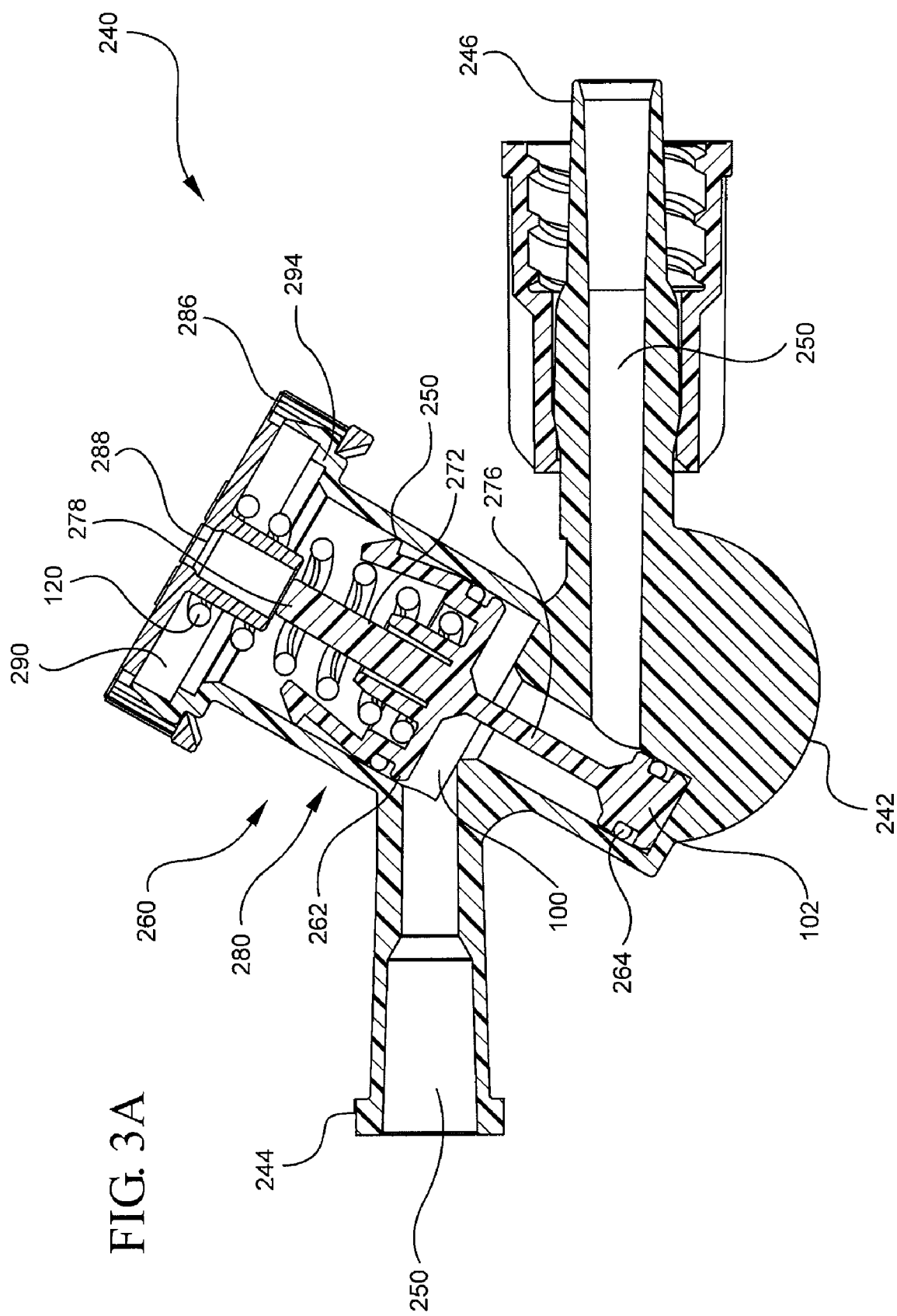
FIG. 3A is a cross-section side view of an inactivated auto-occlusion safety device incorporating a locking mechanism in accordance with a representative embodiment of the present invention.
Figure 3B:
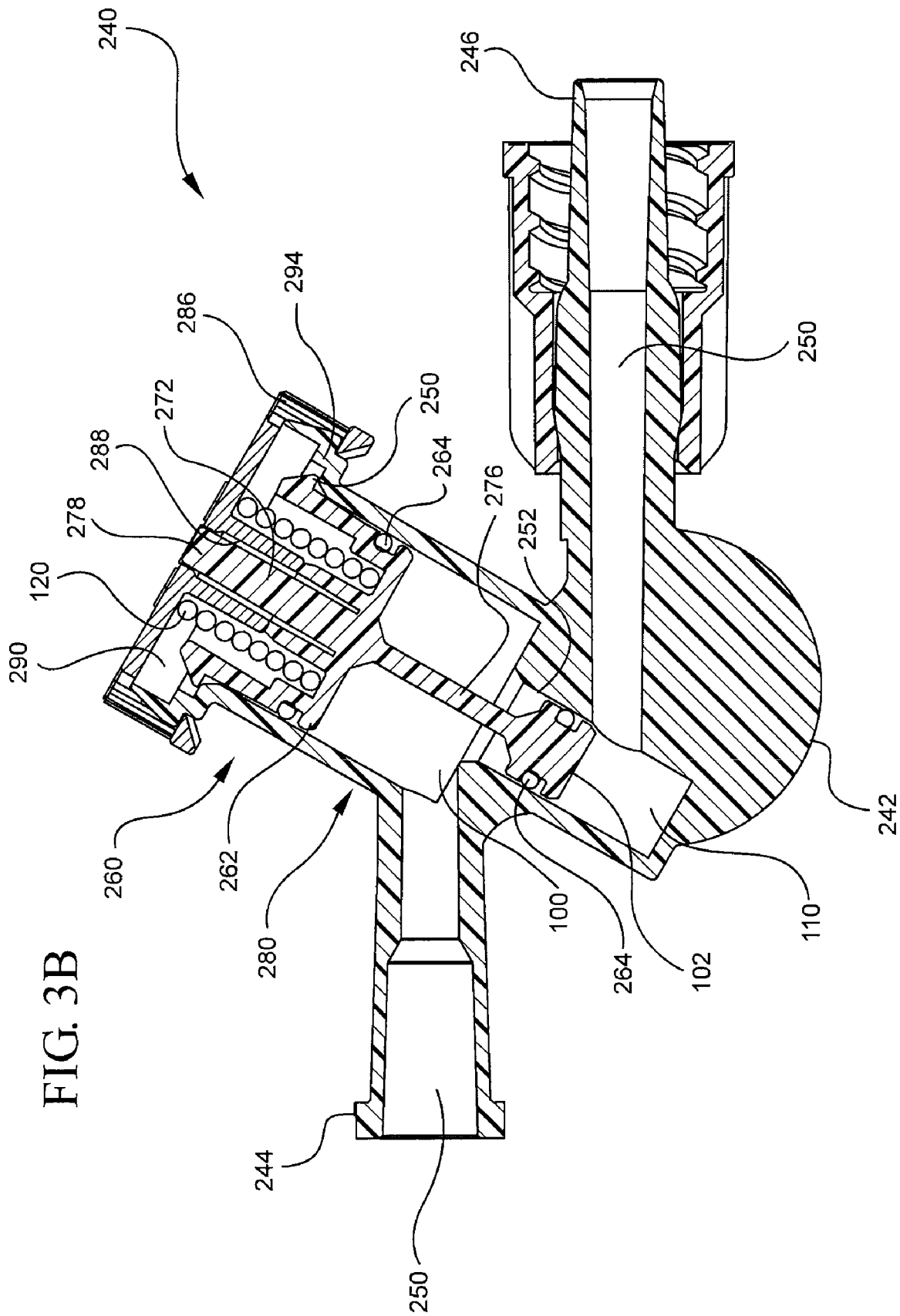
FIG. 3B is a cross-section side view of an activated auto-occlusion safety device incorporating a locking mechanism in accordance with a representative embodiment of the present invention.
Figure 3C:
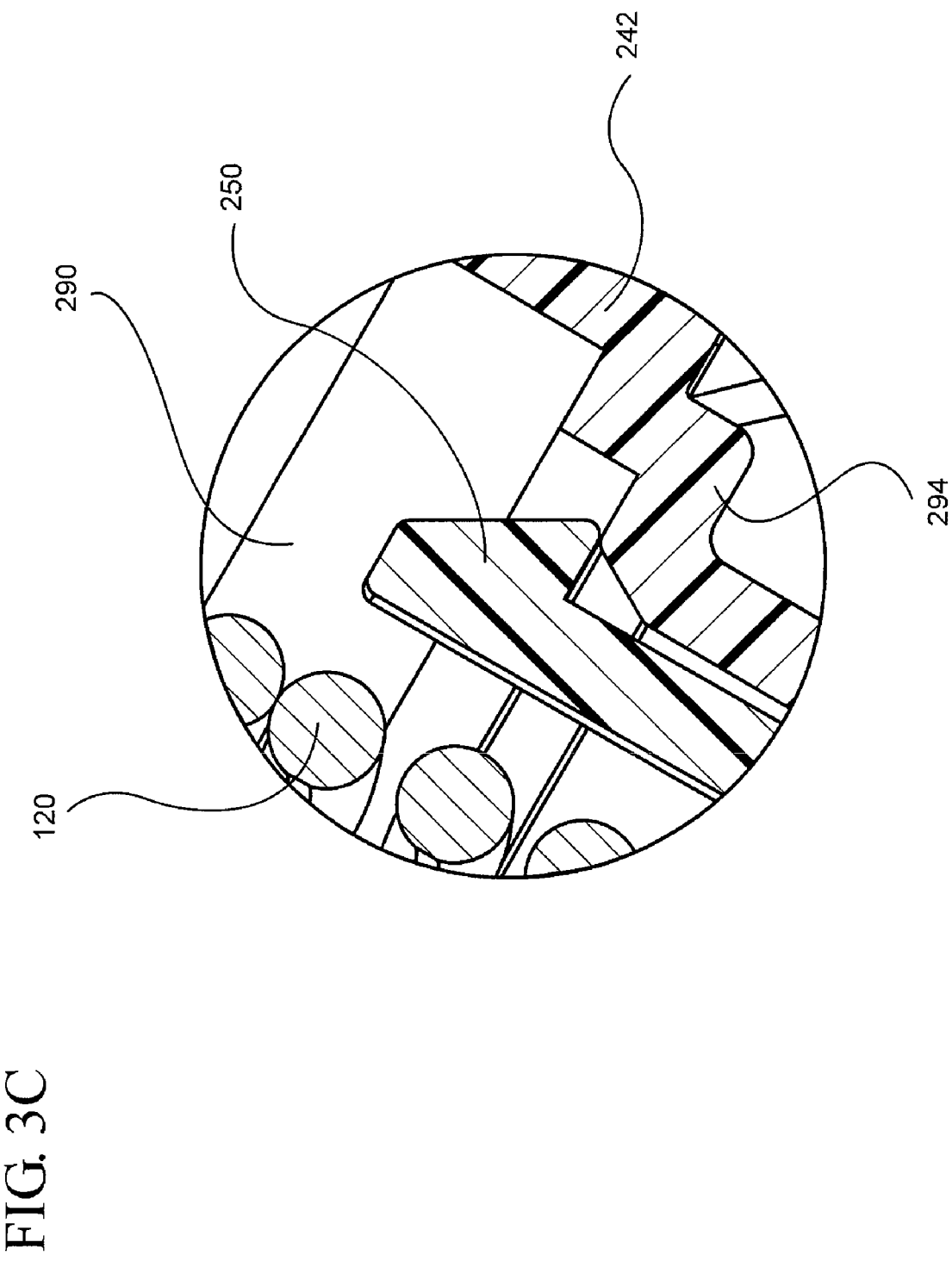
FIG. 3C is a cross-section detail view of an engaged locking mechanism in accordance with a representative embodiment of the present invention.

Referring now to FIG. 3A, a cross-section view of an auto-disabled safety device 240 is shown in an inactivated position. Parts corresponding to those previously described are designated with similar reference numbers beginning with 200. The auto-disabled safety device 240 is similar to the auto-occlusion device 40 of FIGS. 2A and 2B, but is modified to include a locking mechanism 250. The locking mechanism 250 generally comprises an inwardly biased hook or clip feature formed on an upward extended portion of the plunger 262. The locking mechanism is configured and positioned such that when the safety device 240 is activated, the hook or clip feature engages a stepped surface or clip catch 294 of the compression chamber 280 inner wall surface 284 as shown in FIG. 3B, and shown in detail in FIG. 3C. Once engaged, the locking mechanism 250 retains the piston 270 in an activated position. Unlike previous embodiments, when the pressure within the fluid pathway 250 decreases to less than the threshold pressure of the valve 260, the piston 270 remains in an activated position thereby preventing further infusion.

Figure 4A:
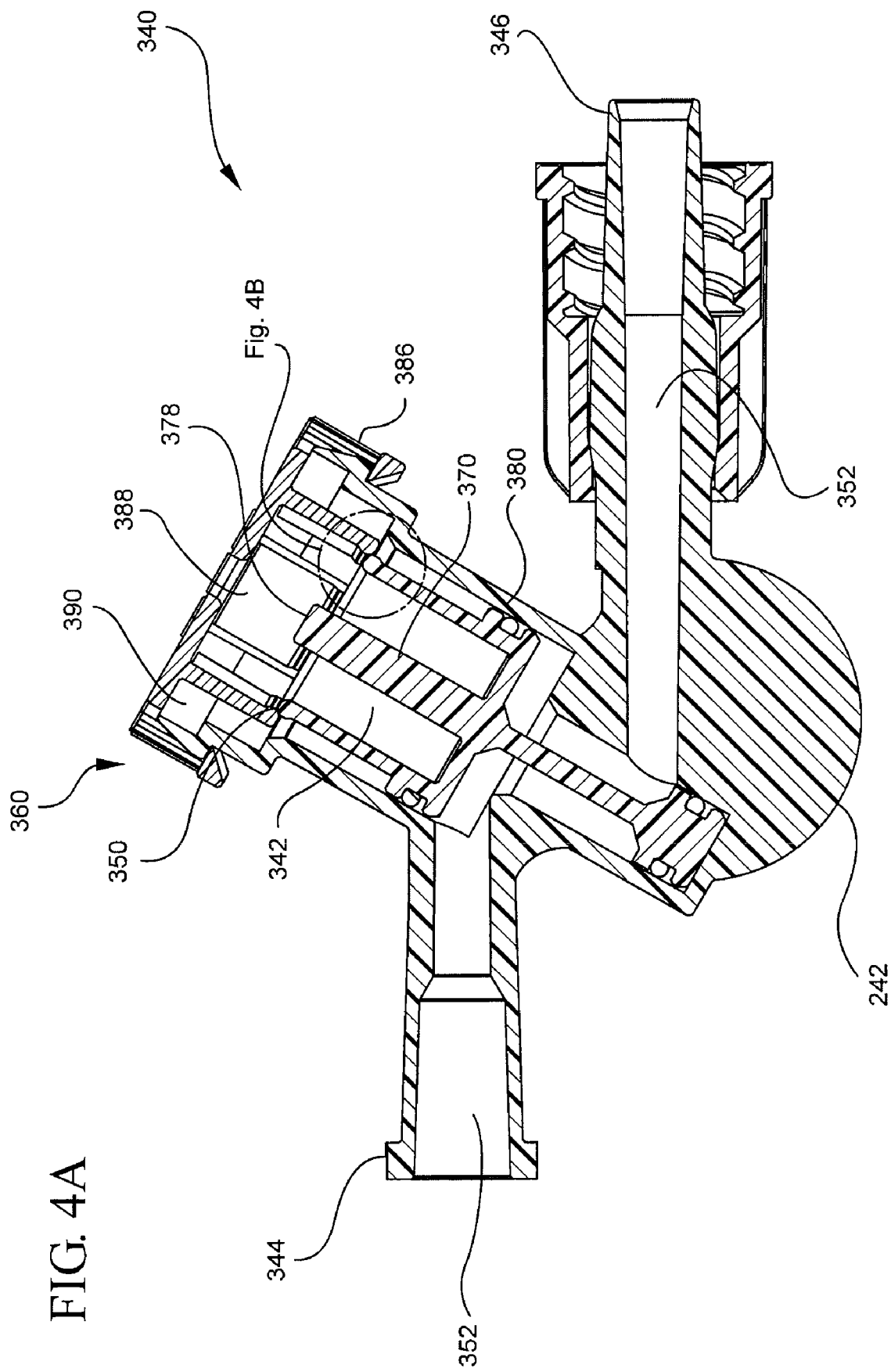
FIG. 4A is a cross-section side view of an inactivated auto-occlusion safety device in accordance with a representative embodiment of the present invention.
Figure 4B:
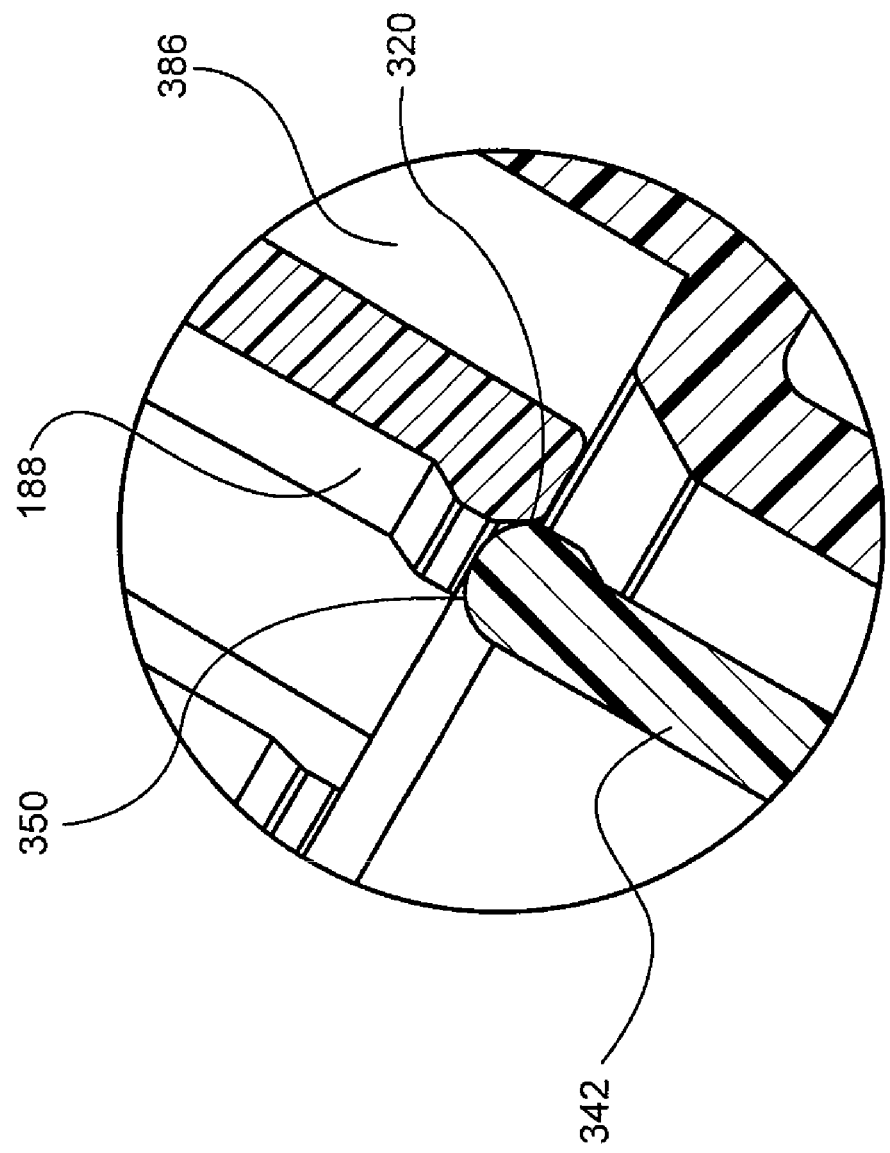
FIG. 4B is a cross-section detail view of an interface between an extended flange of a piston and a shear arm of a lid component in accordance with a representative embodiment of the present invention.
Figure 4C:
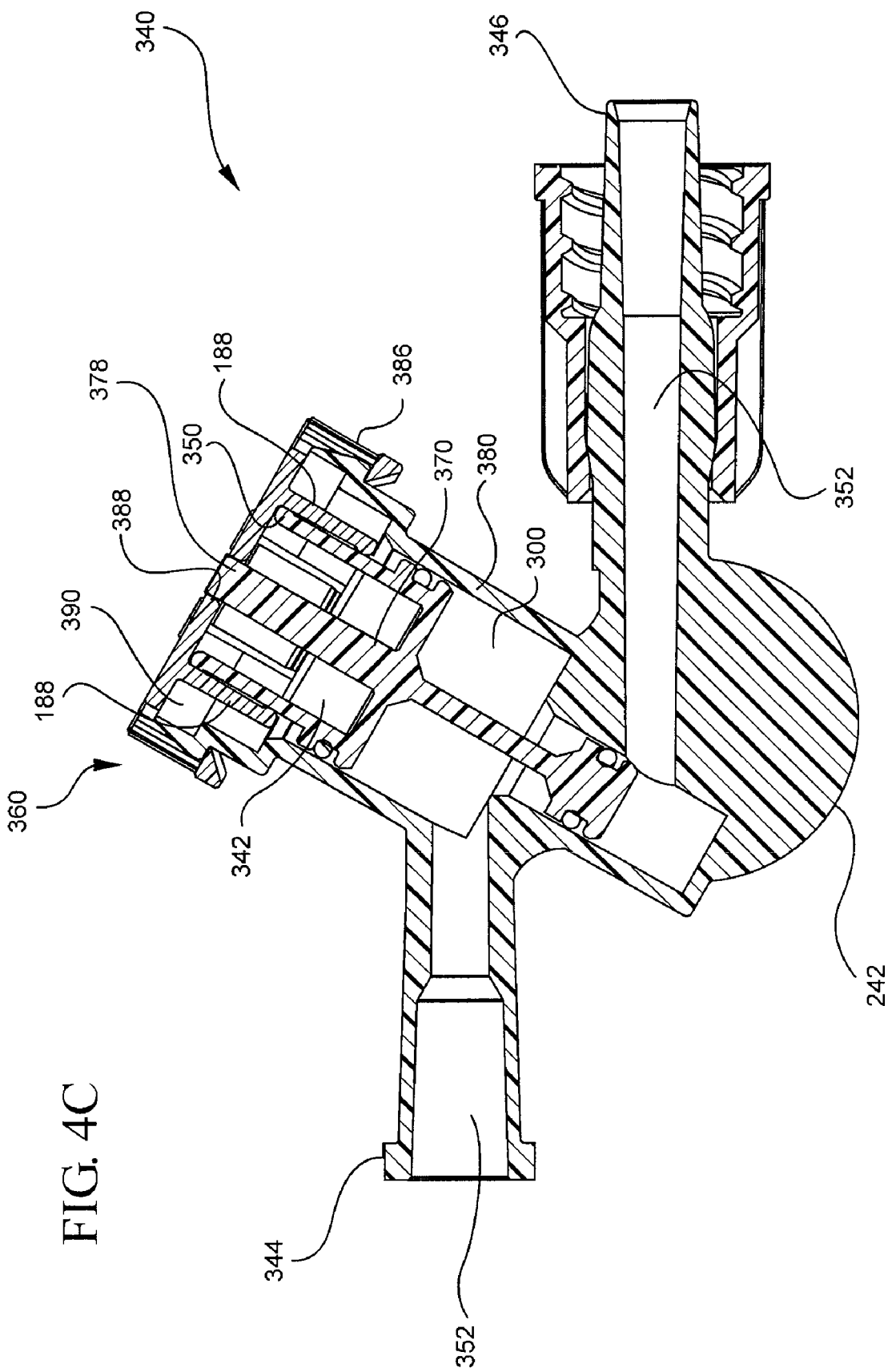
FIG. 4C is a cross-section side view of an activated auto-occlusion safety device in accordance with a representative embodiment of the present invention.
Figure 4D:
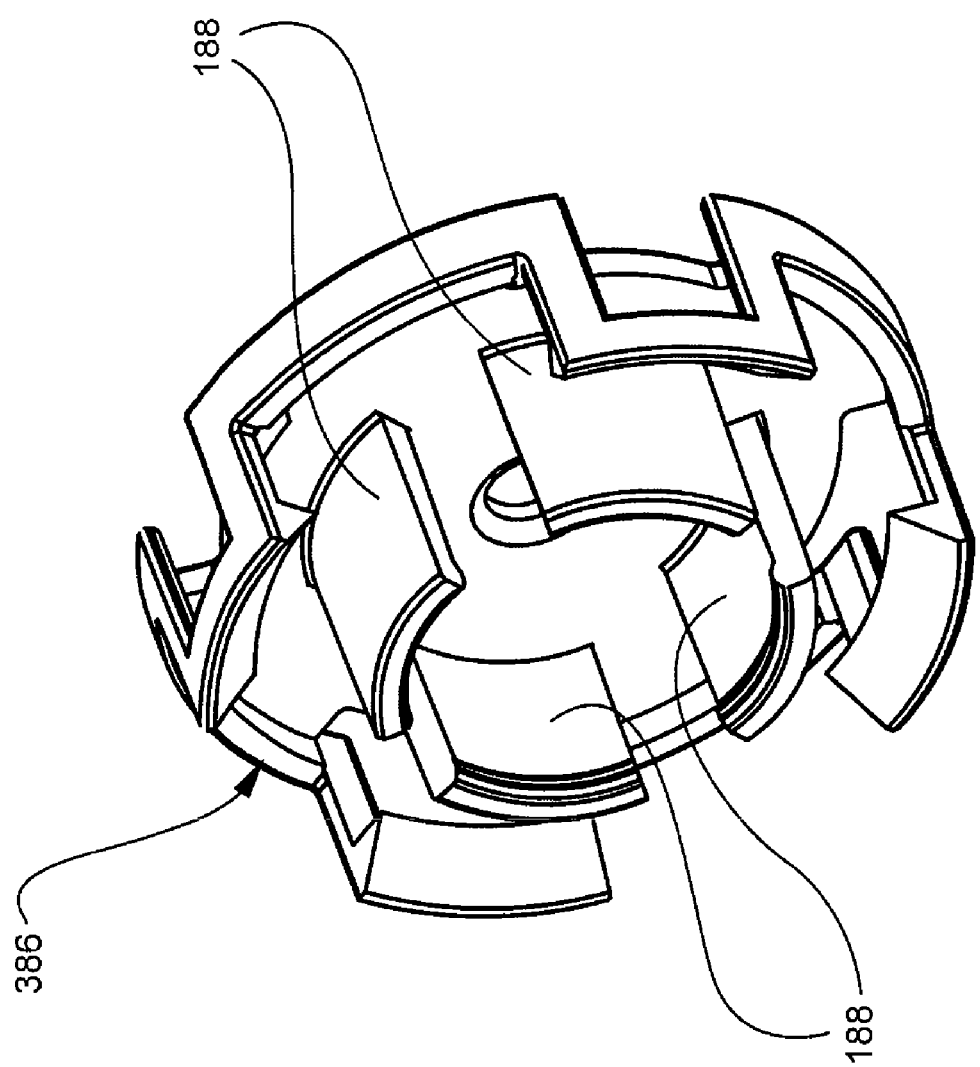
FIG. 4D is a perspective view of a lid component incorporating shear arms in accordance with a representative embodiment of the present invention.

Referring now to FIG. 4A, an auto-occlusion safety device 340 is shown in an inactivated, or open flow position. Parts corresponding to those previously described are designated with similar reference numbers beginning with 300. In this embodiment, the locking mechanism 250 of the previous embodiment is replaced with an extended flange 342 having a leading edge 350. The leading edge 350 is configured to form an interface 320 with a plurality of shear arms 188 extending inwardly from the modified lid 386, as shown in FIGS. 4A and 4B, and shown in detail in FIG. 4B. As the fluid pressure in the fluid pathway 352 exceeds the threshold pressure of the interface 320, the shear arms 188 are biased outwardly and the extended flange 342 moves inwardly past the shear arms 188, as shown in FIG. 4C. Following activation of the valve 360, the extended flange 342 of the piston is wedge between opposing shear arms 188 thereby preventing the piston 370 from returning to an inactivated position. In some embodiments, the shear arms 188 further include a hook feature (not shown) configured to compatibly engage a notch (not shown) formed on an outer surface of the extended flange 342. Thus, when the piston 370 is in an activated position, the hook features and the notches engage one another locking the piston 370 in an activated position.

Figure 5A:
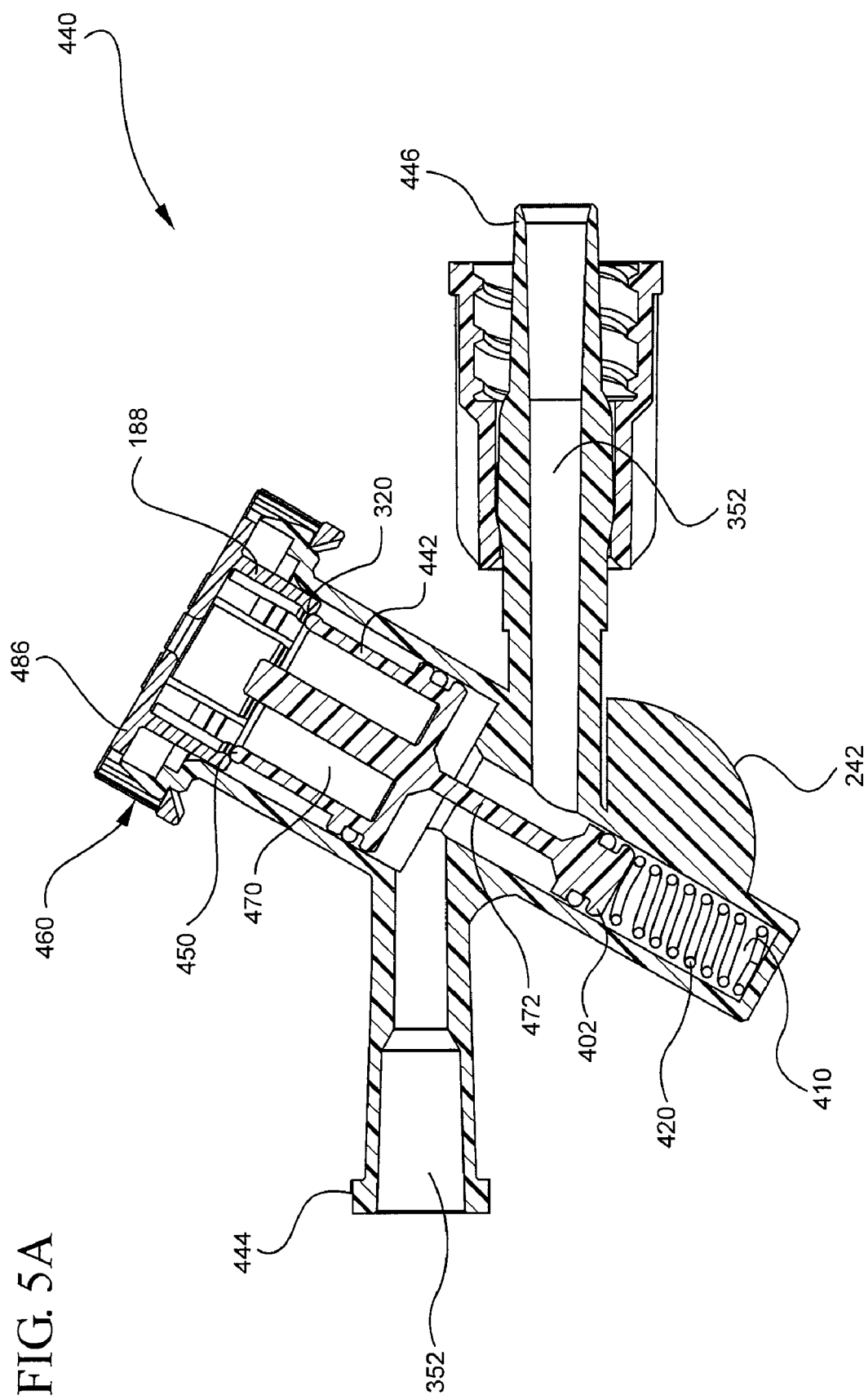
FIG. 5A is a cross-section side view of an inactivated auto-occlusion safety device incorporating an assist spring in accordance with a representative embodiment of the present invention.
Figure 5B:
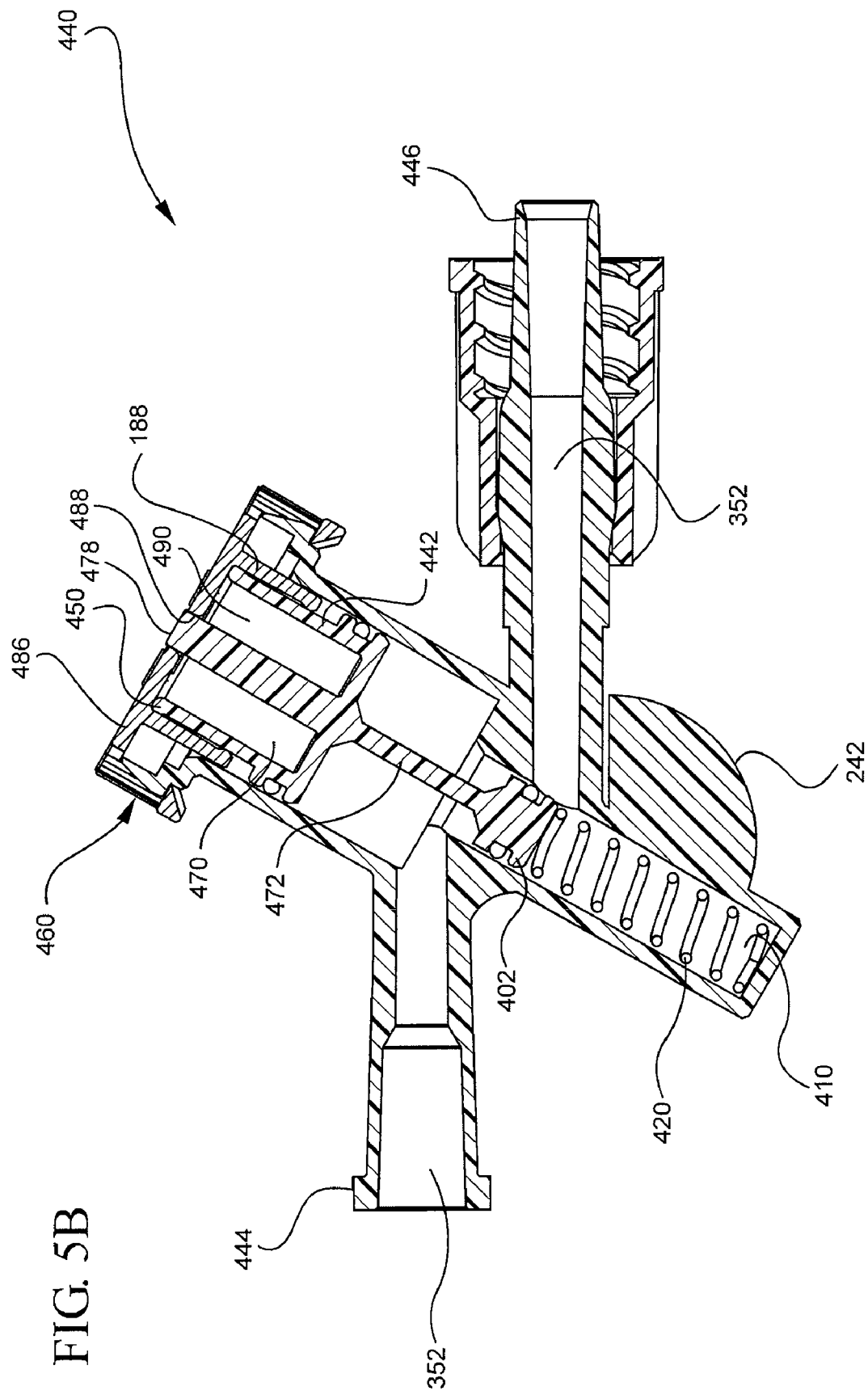
FIG. 5B is a cross-section side view of an activated auto-occlusion safety device incorporating an assist spring in accordance with a representative embodiment of the present invention.

In some embodiments, the safety device 340 further includes a compression spring 420 interposed between the terminal end 402 of the piston 470 and the housing chamber 410, as shown in FIGS. 5A and 5B. Referring now to FIG. 5A, an auto-occlusion safety device 440 is shown in an inactivated or open flow position. Parts corresponding to those previously described are designated with similar reference numbers beginning with 400. A compression spring 420 is positioned within the housing chamber 410 interposed between the terminal end 402 of the piston 470 and the housing chamber 410. The compression spring 420 is compressed so as to provide an initial pressure to the interface 420 between the extended flange 442 and the shear arms 188. Upon activation of the valve 460, the spring 420 is released thereby assisting the repositioning of the piston 470, as shown in FIG. 5B. Thus, the compression spring 420 lessens the time required to reposition the piston 470 to effectuate occlusion of the fluid pathway 450.

Figure 6A:
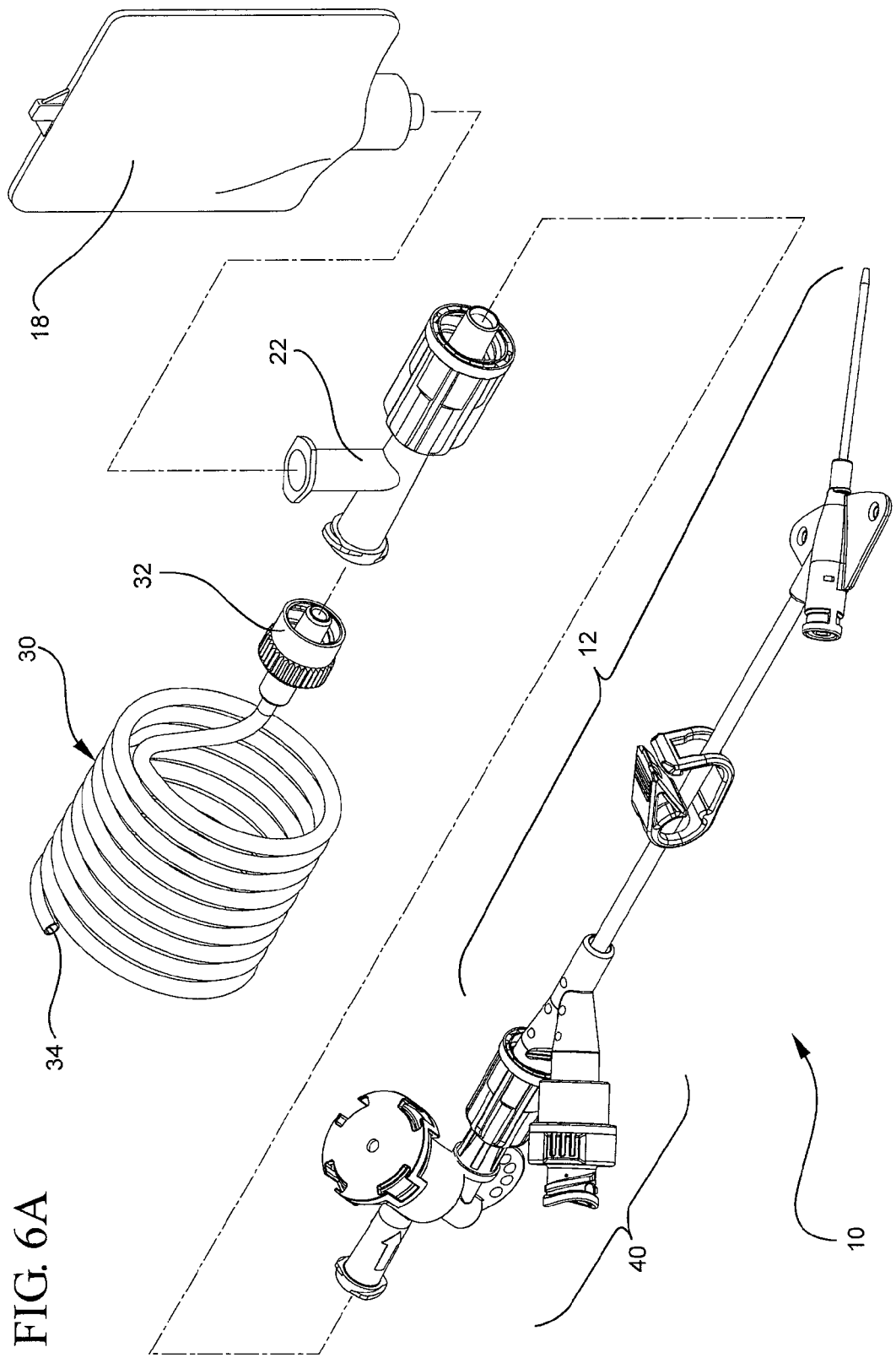
FIG. 6A is a perspective view of an infusion system incorporating an accumulator in accordance with a representative embodiment of the present invention.

Referring now to FIG. 6A, some embodiments of the present invention further include an inline accumulator 18 coupled to the infusion system 10 via a y-adapter 22. An accumulator 18 may include any device capable of diverting and storing an infusant when a fluid pressure within the infusion system 10 exceeds the threshold pressure of the auto-occlusion safety device 40. An accumulator 18 is desirable to prevent rupture of a downstream infusion component 12 during the response time required for activation of the safety device 40.

For example, when a vascular access device 12 becomes kinked or otherwise occluded, upstream pressure increases rapidly to a fluid pressure in excess of the safety device 40 threshold pressure. However, in some instances the fluid pressure increases with such rapidity that the safety device 40 is unable to be completely activated prior to internal pressures exceeding rupture tolerances of downstream components. Thus, infusion components may rupture prior to complete activation of the safety device 40. Therefore, in some embodiments it is desirable to include an accumulator 18 in the infusion system 10.

Figure 6B:
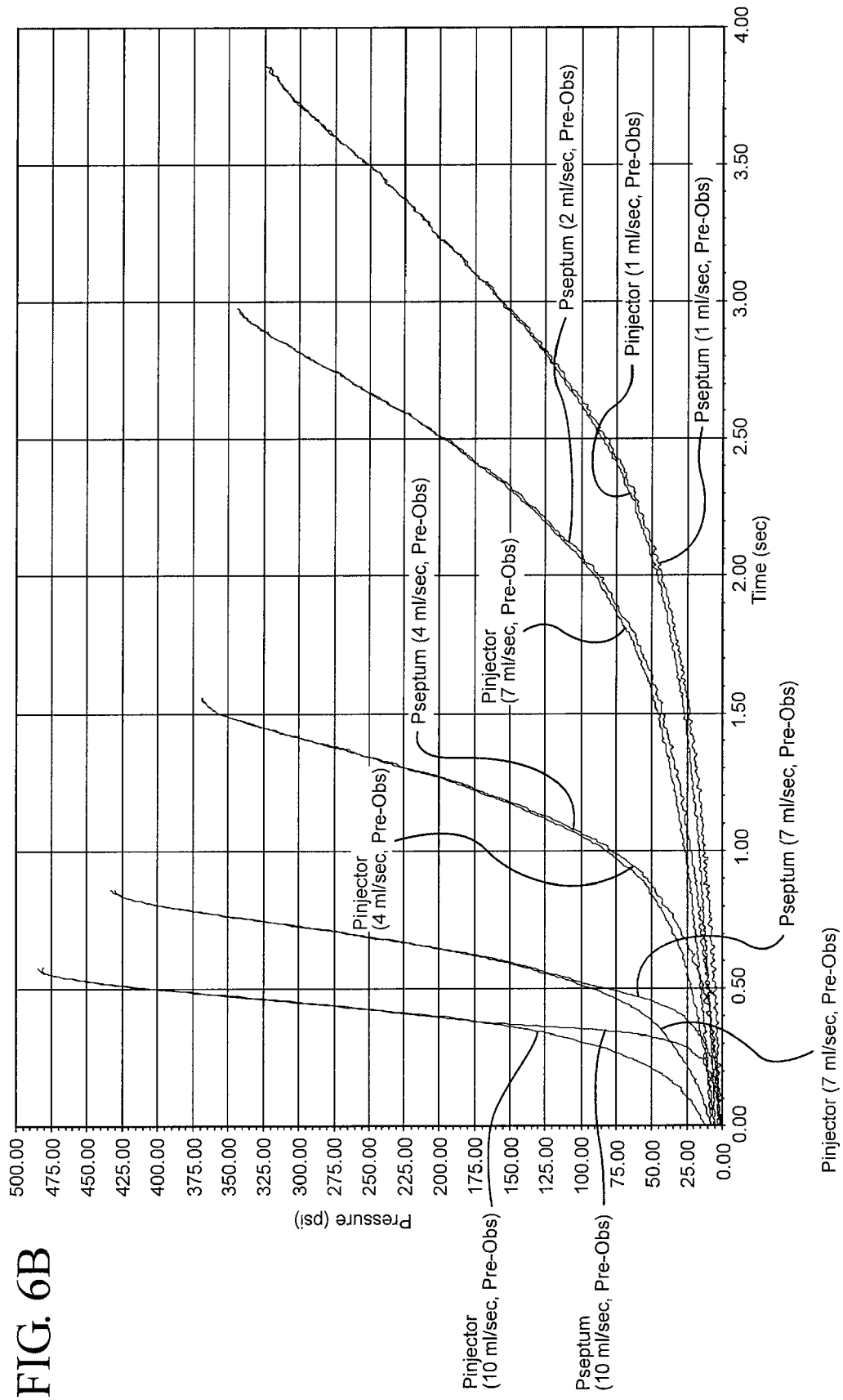
FIGS. 6B-6D are various charts demonstrating pressure response times for various occluded infusion components in accordance with representative embodiments of the present invention.
Figure 6C:
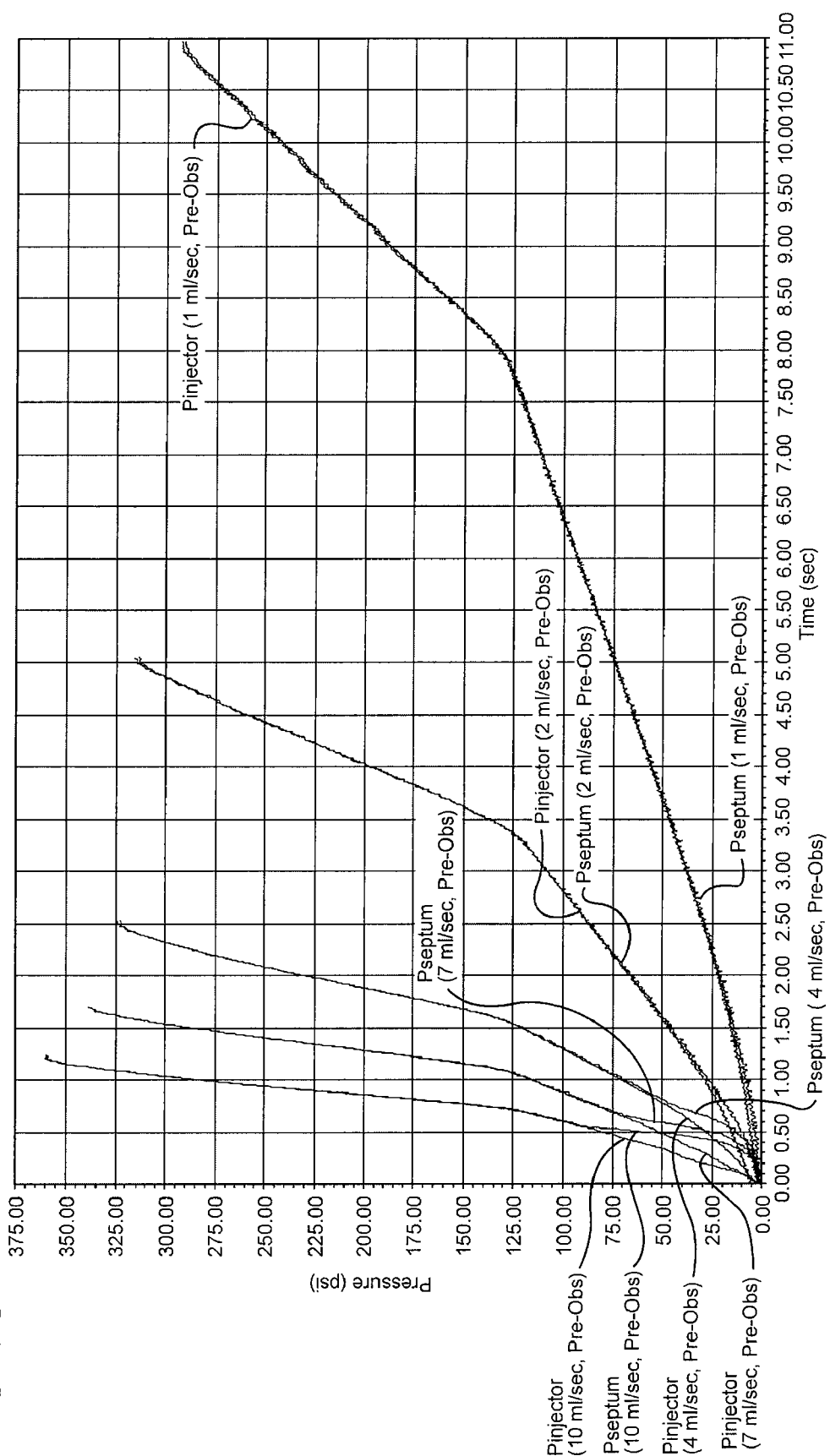
Figure 6D:
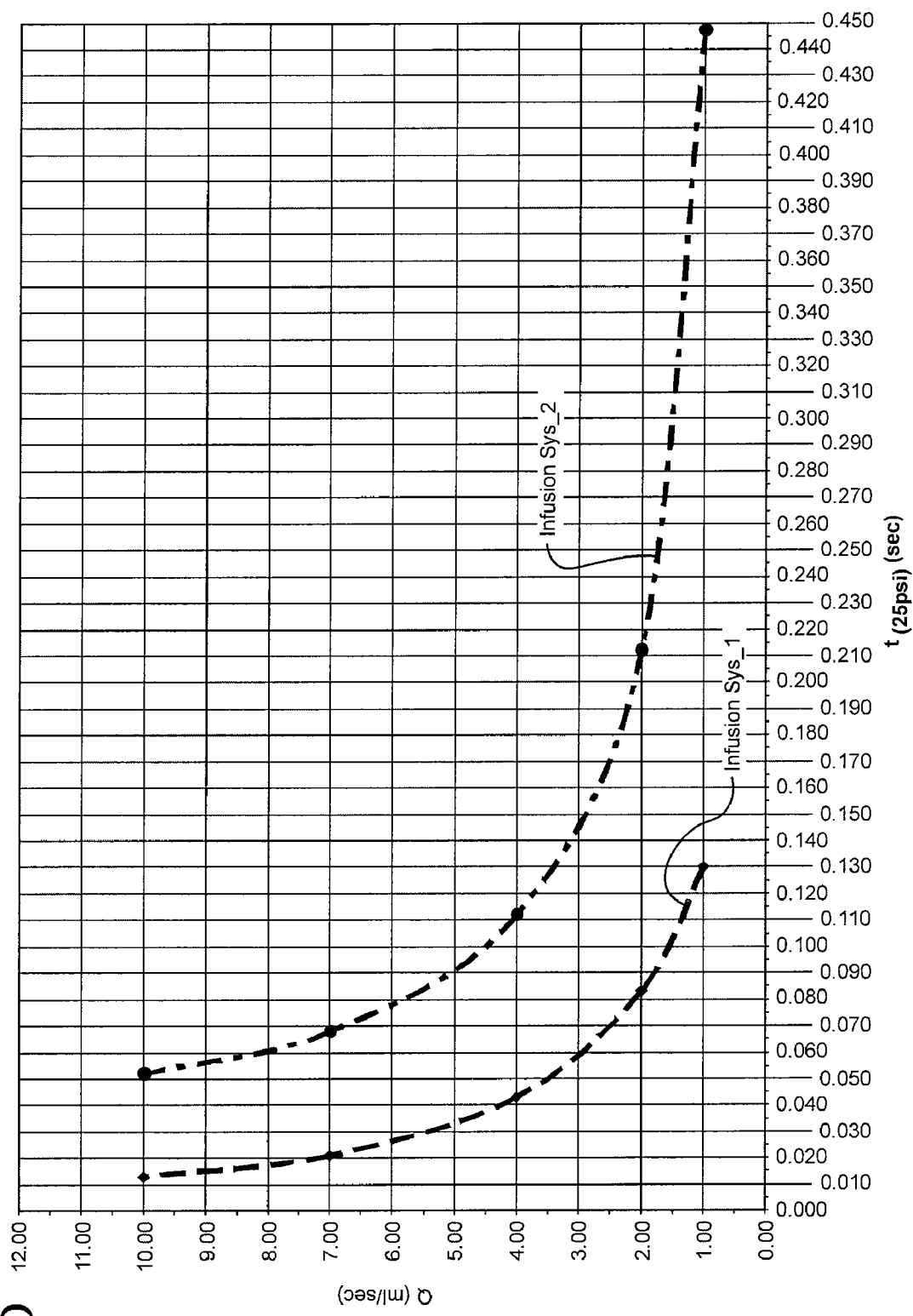

Referring now to FIGS. 6B-6D, various graphs are shown demonstrating the time required for fluid pressures to increase within an occluded infusion system for a given flow rate and a given viscosity. In several experiments, fluid pressures within the occluded infusion system exceeded 300 psi in less than a second. Thus, for these combinations of injection pump, infusion component and flow rate, the valve 60 of the safety device 40 must activate completely in less than one second to avoid possible component rupture.

Therefore, an accumulator 18 may be desirable where a threshold pressure of the accumulator 18 is less than a threshold pressure of the safety device 40. For example, if a rupture tolerance for an infusion system is 350 psi, and a threshold pressure for a safety device is 300 psi, then a desirable threshold pressure for an accumulator 18 may be 225 psi. In this example, a rapidly increasing fluid pressure within the infusion system would activate the accumulator 18 just prior to activating the safety device 40. Thus, in the time required for the safety device 40 to react to the rapid increase in fluid pressure, excess fluid and pressure are diverted into the accumulator 18 thereby preventing pressure buildup in excess of the rupture tolerance.

Figure 6F:
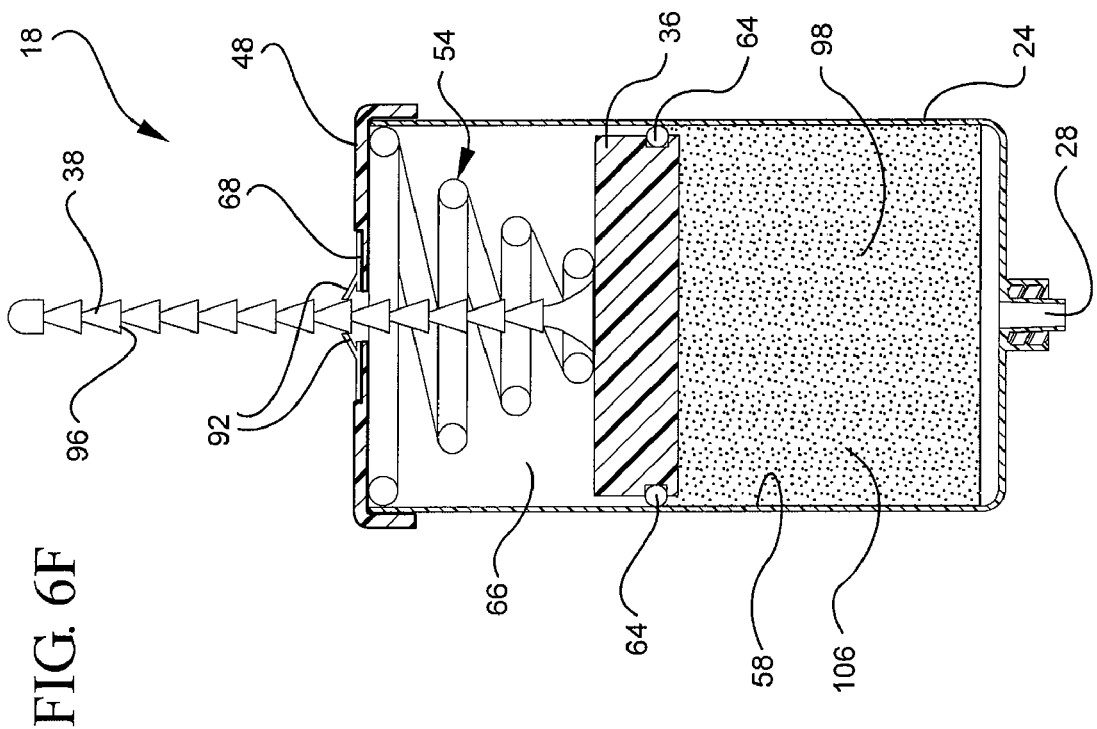
FIG. 6F is a cross-section side view of an activated accumulator and retained infusant in accordance with a representative embodiment of the present invention.
Figure 6E:
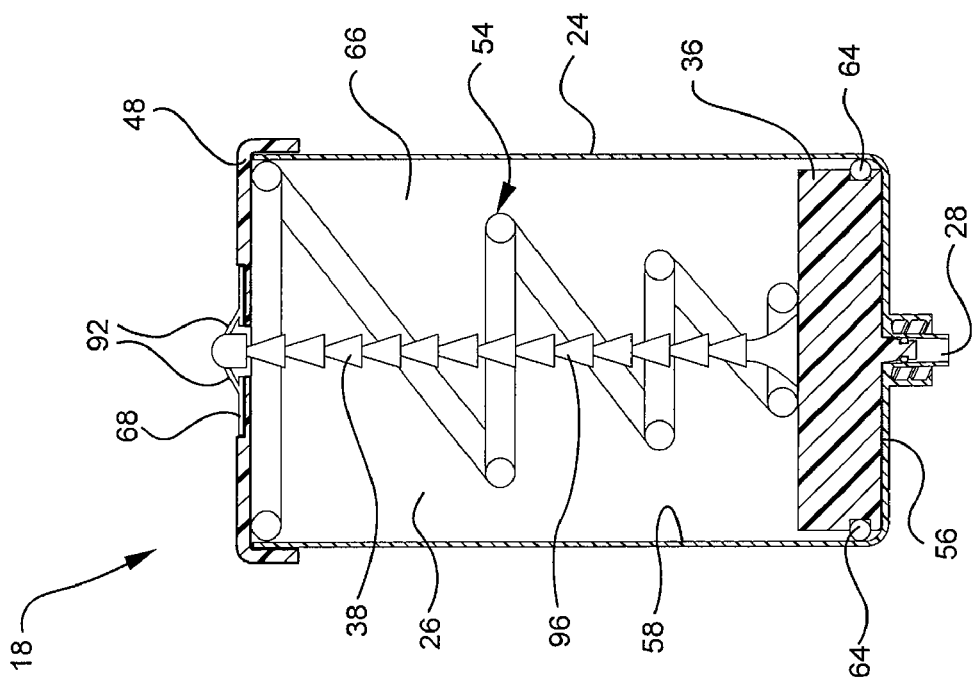
FIG. 6E is a cross-section side view of an inactivated accumulator in accordance with a representative embodiment of the present invention.

Referring now to FIG. 6E, an accumulator 18 is shown prior to activation of the safety device 40. The accumulator 18 generally comprises an outer casing 24 having an inner lumen defining a compression chamber 26. The casing 24 further comprises an inlet port 28 configured to couple to the infusion system via a luer lock on a y-port 22, or another point of access. A plunger 36 is disposed within the compression chamber 26 and is coupled to an indicator rod 38 which extends through a lid 48 of the compression chamber 26. A compression spring 54 is further interposed between the plunger 36 and the lid 48 so as to bias the plunger 36 against a base surface 56 of the accumulator 18.

In some embodiments, a seal 64 is interposed between the plunger 36 and an inner wall surface 58 of the compression chamber 26 so as to prevent an infusant within the fluid pathway 50 from bypassing the plunger 36 into the upper chamber 66 of the compression chamber 26. In some embodiments, the seal 64 is an o-ring inserted into a groove circumscribing an outer perimeter of the plunger 36.

In some embodiments, the lid 48 comprises a metallic material, such as steel, and further includes retention lock clip 68. The retention lock clip 68 comprises an annular washer having a pair of clips 92 that compatibly engage a ridged surface 96 of the indicator rod 38. As an infusant 106 is diverted into the accumulator 18, the plunger 36 is driven upward towards the lid 48 and the indicator rod 38 further extends outwardly from the lid 48, as shown in FIG. 6F. As the lower chamber 98 of the accumulator 18 fills with infusant 106, the plunger 36 rises and compresses the compression spring 54 between the plunger 36 and the lid 48. The ridged surface 96 of the indicator rod 38 permits one-way passage of the indicator rod 38 through the retention lock clip 68. Thus, as the fluid pressure within the infusion system 10 decreases to a pressure less than the threshold pressure of the accumulator 18, the extended position of the indicator rod 38 is maintained, thereby signaling to the user that the infusion procedure was unsuccessful. The interaction between the indicator rod 38 and the retention clip 68 further prevent reuse of the accumulator 18 for subsequent infusion procedures.

In some embodiments, an accumulator 18 is provided without a retention lock clip 92. Instead, the compression spring 54 is permitted to return the plunger 36 to an inactivated position following a decrease of fluid pressure within the infusion system 10. As the plunger 36 is returned to its inactivated position, infusant 106 within the lower chamber 98 of the compression chamber 26 is pushed back into the system 10 and infused into the patient.

Figure 7A:
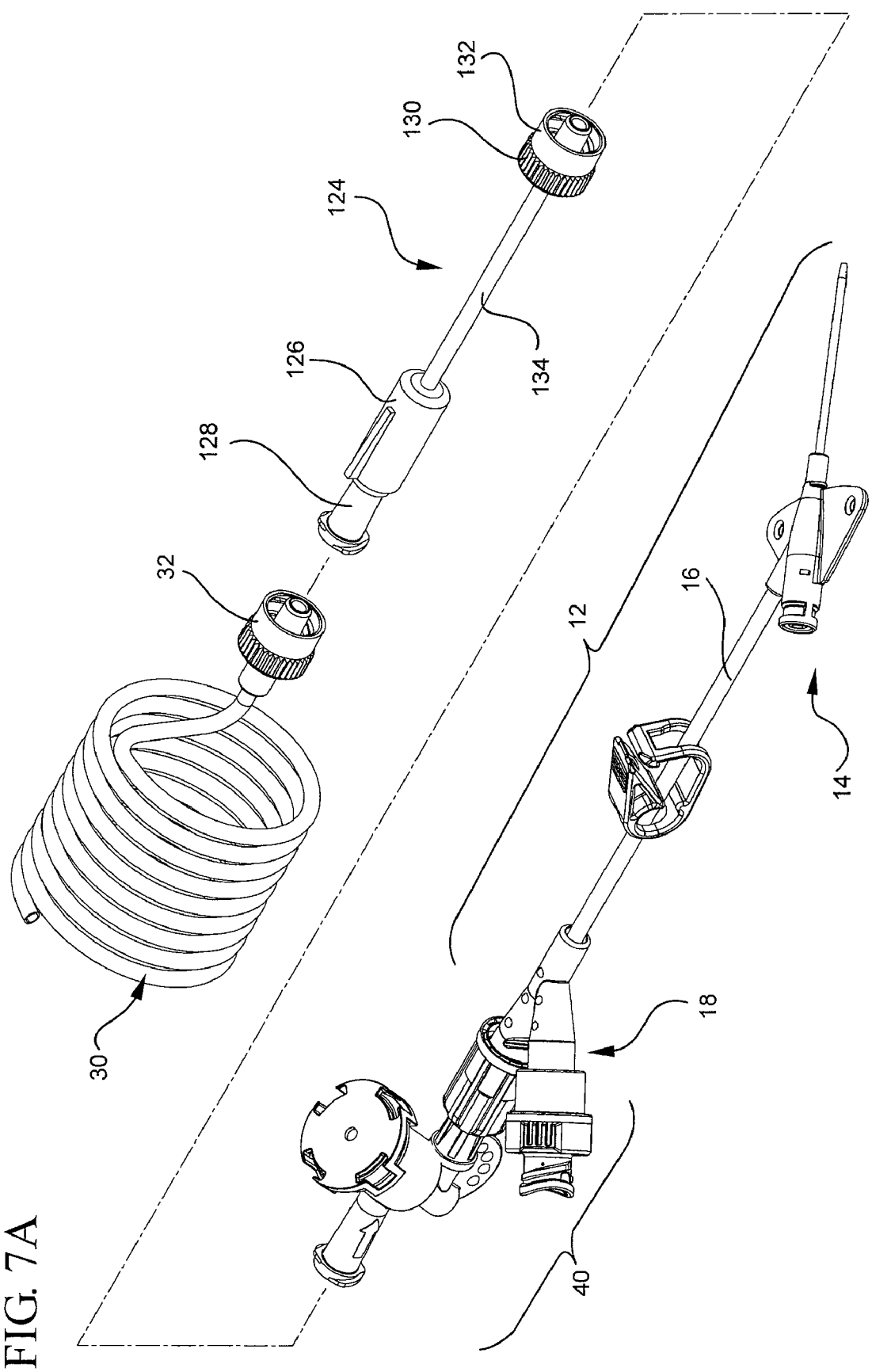
FIG. 7A is a perspective view of an infusion system incorporating a bladder accumulator in accordance with a representative embodiment of the present invention.

Referring now to FIG. 7A, an infusion system 10 may further include a bladder accumulator 124. A bladder accumulator 124 generally comprises a first end 126 having a first coupler 128 for connecting the accumulator 124 to an upstream component 30, and a second end 130 having a second coupler 132 for connecting the accumulator 124 to a downstream component 40. The accumulator further comprises a hollow bladder 134 interposedly positioned between the first end 126 and the second end 130. The bladder 134 generally comprises a flexible, elastic material that is compatible with infusion procedures. For example, in some embodiments the bladder 134 comprises a latex material. In other embodiments, the bladder 134 comprises a rubber material. Finally, in some embodiments the bladder comprises Tygon® tubing.

Figure 7B:
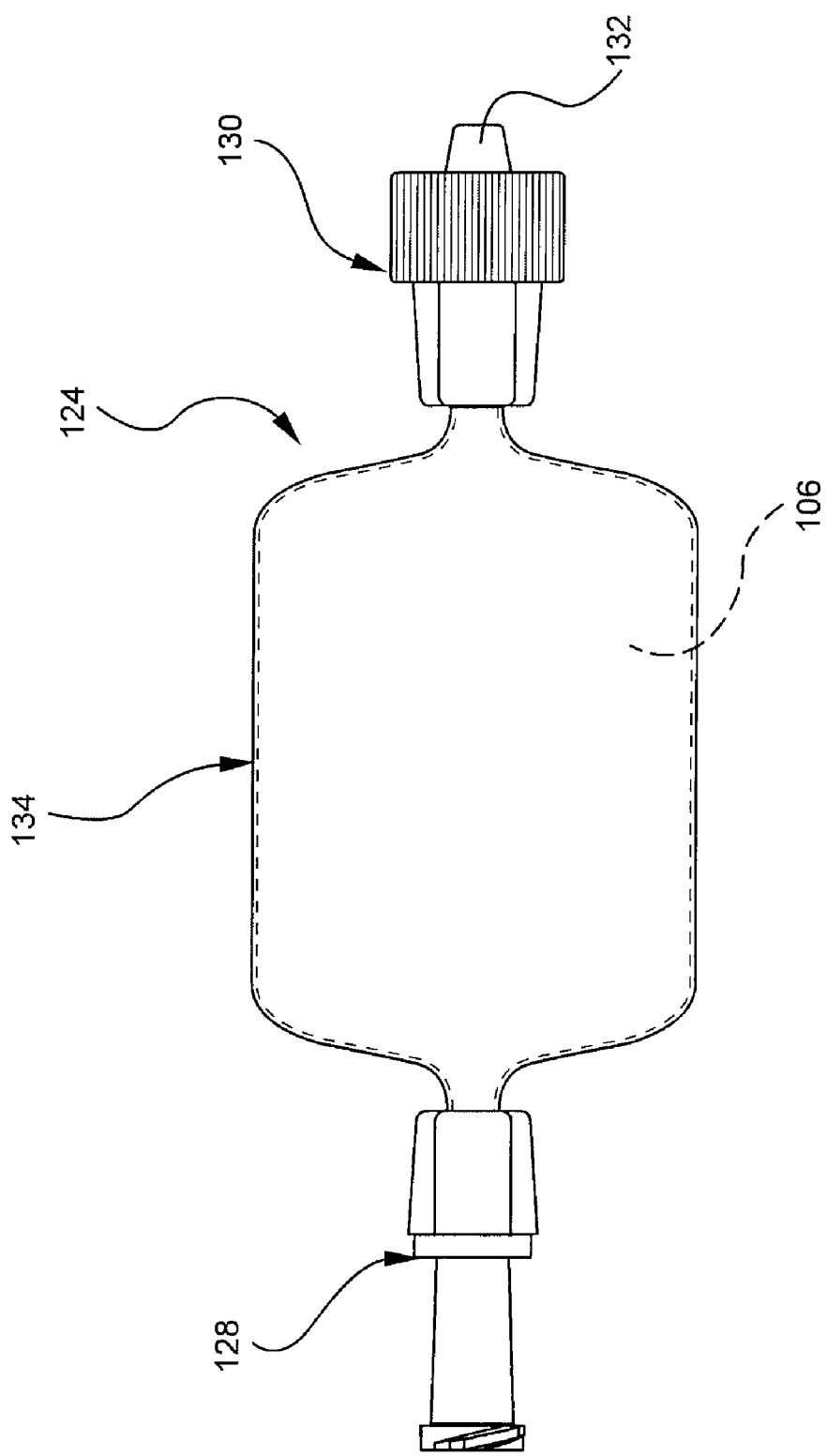
FIG. 7B is a perspective view of an activated accumulator in accordance with a representative embodiment of the present invention.

As previously discussed, an accumulator is provided to divert and store excess infusant within an infusion system 10, thereby reducing a rapidly increasing fluid pressure within the system 10. As fluid pressure increases with an infusion system 10, the bladder portion 134 of the accumulator 124 begins to fill with excess infusant 106. The elastic properties of the bladder 134 permit the volume of the bladder 134 to increase as needed to accommodate excess infusant 106, as shown in FIG. 7B. As the fluid pressure within the system decreases, the bladder 134 resumes its inactivated volume thereby displacing excess infusant 106 to infusion components downstream. Thus, in some embodiments it is desirable to incorporate an accumulator 124 into an infusion system 10, where a threshold pressure of the accumulator 124 is less than a rupture tolerance of the infusion system, and less than a threshold pressure of a safety device 40.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A safety device for occluding a flow through a vascular access system, the safety device comprising:
a casing having an inlet port and an outlet port;
a fluid pathway in communication with the inlet port and the outlet port;
an occlusion valve interposed between the inlet port and the outlet port, the occlusion valve having an inactivated position and an activated position, the occlusion valve further comprising a piston having a first end slidably positioned in a compression chamber, a clip forming a terminal end portion of the piston, and a clip catch forming a terminal end portion of an inner wall surface of the compression chamber, the compression chamber directly abutting the fluid pathway, and the piston having a second end slidably positioned in a housing chamber, a seal being formed between the second end and the housing chamber in the inactivated position, wherein upon activation of the occlusion valve, the piston translates within the compression chamber from the inactivated position to the activated position, the clip and the clip catch interlocking and irreversibly retaining the piston in the activated position, whereby the second end of the piston occludes the fluid pathway.

2. The safety device of claim 1, wherein the activation of the occlusion valve is automatic.

3. The safety device of claim 1, further comprising:
a compression chamber configured to house a first portion of the occlusion valve; and
a housing chamber configured to house a second portion of the occlusion valve, the second portion of the occlusion valve being configured to leave the housing chamber and occlude the fluid pathway upon activation of the occlusion valve.

4. The safety device of claim 1, further comprising a compression spring disposed between a portion of the piston and an inner wall surface of the compression chamber, wherein the compression spring biases the second end of the piston into the housing chamber.

5. The safety device of claim 1, further comprising a seal interposed between an outer surface of the piston and an inner wall surface of the compression chamber.

6. The safety device of claim 5, further comprising a fluid inlet in fluid communication with the fluid channel and the compression chamber.

7. The safety device of claim 1, further comprising an indicator to signal an activated position of the occlusion valve.

8. The safety device of claim 1, further comprising a leading edge forming a terminal end portion of the piston, and a finger forming a portion of the compression chamber, a tip portion of the finger abutting the leading edge to maintain the second end of the piston within the housing chamber, wherein a pressure within the fluid pathway that exceeds the threshold pressure of the occlusion valve defeats the interface between the leading edge and the finger to enable activation of the occlusion valve.

9. The safety device of claim 8, further comprising a compression spring interposed between the piston and the housing chamber, wherein upon activation of the occlusion valve the compression spring biases the piston into the activated position.

10. The safety device of claim 1, further comprising an accumulator coupled to a portion of the inlet port and in fluid communication with the fluid pathway.

11. The safety device of claim 1, further comprising a t-shape configuration.

12. The safety device of claim 1, further comprising a z-shape configuration.

13. The safety device of claim 10, wherein the accumulator provides time for the device to actuate.

14. A high pressure infusion system, comprising:
a vascular access device forming a first end of the high pressure infusion system;
an injector forming a second end of the high pressure infusion system;
an in-line safety device interpose between the vascular access device and the injector pump, the in-line safety device forming a middle section of the high pressure infusion system, and including an occlusion valve; and
a fluid pathway in communication with the vascular access device, the in-line safety device, and the injector pump, wherein the occlusion valve comprises a piston having an inactivated position and an activated position, the piston further having a first end slidably positioned in a compression chamber, the compression chamber directly abutting the fluid pathway, and a second end slidably positioned in a housing chamber, a seal being formed between the second end and the housing chamber in the inactivated position, wherein upon activation of the in-line safety device, the piston translates within the compression chamber to the activated position whereby the second end of the piston occludes the fluid pathway.

15. The system of claim 14, further comprising:
a compression chamber configured to house a first portion of the occlusion valve; and
a housing chamber configured to house a second portion of the occlusion valve, the second portion of the occlusion valve being configured to leave the housing chamber and occlude the fluid pathway upon activation of the in-line safety device.

16. The system of claim 15, further comprising a compression spring disposed between a portion of the piston and an inner wall surface of the compression chamber, wherein the compression spring biases the second end of the piston into the housing chamber.

17. The system of claim 15, further comprising a seal interposed between an outer surface of the piston and an inner wall surface of the compression chamber.

18. The system of claim 17, further comprising a fluid inlet in fluid communication with the fluid channel and the compression chamber.

19. The system of claim 15, further comprising a clip forming a terminal end portion of the piston, and a clip catch forming a terminal end portion of an inner wall surface of the compression chamber, wherein upon activation of the in-line safety device, the clip and the clip catch interlock and irreversibly retain the piston in the activated position.

20. The system of claim 14, further comprising an indicator to signal an activated position of the occlusion valve.

21. The system of claim 15, further comprising a leading edge forming a terminal end portion of the piston, and a finger forming a portion of the compression chamber, a tip portion of the finger abutting the leading edge to maintain the second end of the piston within the housing chamber, wherein a pressure within the fluid pathway that exceeds the threshold pressure of the occlusion valve defeats the interface between the leading edge and the finger to enable activation of the in-line safety device.

22. The system of claim 21, further comprising a compression spring interposed between the piston and the housing chamber, wherein upon activation of the in-line safety device the compression spring biases the piston into the activated position.

23. The system of claim 14, further comprising an accumulator coupled to a portion of the in-line safety device and in fluid communication with the fluid pathway.

24. The system of claim 14, wherein the in-line safety device comprises a t-shape configuration.

25. The system of claim 14, wherein the in-line safety device comprises a z-shape configuration.

26. A method for occlusion of a fluid pathway through an infusion system, the method comprising:
providing a vascular access device configured to access a vasculature system of a patient;
coupling an injector to the vascular access device; and
interposing an in-line safety device between the vascular access device and the injector, wherein the vascular access device, the injector and the in-line safety device are in fluid communication, and wherein the in-line safety device includes an occlusion valve wherein the occlusion valve comprises a piston having an inactivated position and an activated position, the piston further having a first end slidably positioned in a compression chamber, the compression chamber directly abutting the fluid pathway, and a second end slidably positioned in a housing chamber, a seal being formed between the second end and the housing chamber in the inactivated position, wherein upon activation of the occlusion valve, the piston translates within the compression chamber to the activated position whereby the second end of the piston occludes the fluid pathway.

27. The method of claim 26, further comprising coupling an accumulator to a portion of the infusion system in communication with the fluid pathway.

* * * * *